United States Patent [19]

Schmidt et al.

[11] Patent Number: 5,171,854
[45] Date of Patent: Dec. 15, 1992

[54] SUBSTITUTED VINYLCEPHALOSPORINS

[75] Inventors: Gunter Schmidt; Karl G. Metzger, both of Wuppertal; Hans-Joachim Zeiler, Velbert; Rainer Endermann, Wuppertal; Ingo Haller, Wuppertal, all of Fed. Rep. of Germany

[73] Assignee: Bayer Aktiengesellschaft, Leverkusen, Fed. Rep. of Germany

[21] Appl. No.: 534,791

[22] Filed: Jun. 7, 1990

Related U.S. Application Data

[63] Continuation-in-part of Ser. No. 190,901, May 6, 1988, abandoned, and a continuation-in-part of Ser. No. 193,313, May 11, 1988, abandoned.

[30] Foreign Application Priority Data

| May 26, 1987 | [DE] | Fed. Rep. of Germany | 3717663 |
| May 26, 1987 | [DE] | Fed. Rep. of Germany | 3717664 |
| Oct. 8, 1987 | [DE] | Fed. Rep. of Germany | 3734004 |
| Oct. 8, 1987 | [DE] | Fed. Rep. of Germany | 3734005 |

[51] Int. Cl.$^5$ .................. C07D 501/22; A61K 31/545
[52] U.S. Cl. ..................... 540/222; 540/225; 540/227
[58] Field of Search ............. 540/222; 514/202

[56] References Cited

U.S. PATENT DOCUMENTS

| 4,255,423 | 3/1981 | Beattie et al. | 424/246 |
| 4,619,925 | 10/1986 | Hoshi et al. | 514/200 |
| 4,734,407 | 3/1988 | Schmidt et al. | 540/222 |
| 4,748,163 | 5/1988 | Schmidt et al. | 540/222 |
| 4,757,065 | 7/1988 | Angerbauer et al. | 540/222 |

Primary Examiner—Nicholas S. Rizzo
Attorney, Agent, or Firm—Sprung Horn Kramer & Woods

[57] ABSTRACT

β-Lactam compounds of the formula

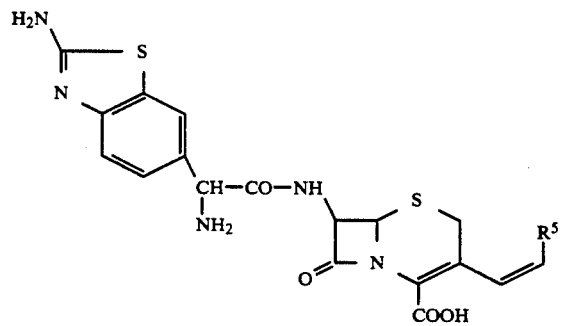

wherein $R^5$ represent cyclopropyl or methyl, useful as antibiotics.

2 Claims, No Drawings

SUBSTITUTED VINYLCEPHALOSPORINS

This is a continuation-in-part of application Ser. No. 190,901, filed May 6, 1988, now abandoned, and of application Ser. No. 193,313, filed May 11, 1988, now abandoned.

It is known that various representatives of 7-α-aminoacylcephalosporins with different substituents in the 3-position of the molecule, thus, for example, cephalexin [7-(D-α-phenylglycylamido)-3-methyl-3-cephem-4-carboxylic acid, compare DE-OS (German Published Specification) 2,432,485], cefaclor [7-(D-α-phenylglycylamido)-3-chloro-3-cephem-4-carboxylic acid, compare DE-OS (German Published Specification) 2,408,698 and 2,728,578] and cefadroxil [7-(D-α-p-hydroxyphenylglycylamido)-3-methyl-3-cephem-4-carboxylic acid, compare DE-OS (German Published Specification) 2,718,741] have a good antibiotic activity.

3-Alkenyl-substituted cephalosporins are furthermore described as compounds with an oral action in DE-OS (German Published Specification) 3,402,642 and U.S. Pat. No. 4,619,925.

Benzothiazolylglycylamido-substituted vinylcephalosporins are known from DE-OS (German Published Specification) 3,508,258. The present invention relates to a selection of the substances described in DE-OS (German Published Specification) 3,508,258.

The invention thus relates to β-lactam compounds of the general formula (I)

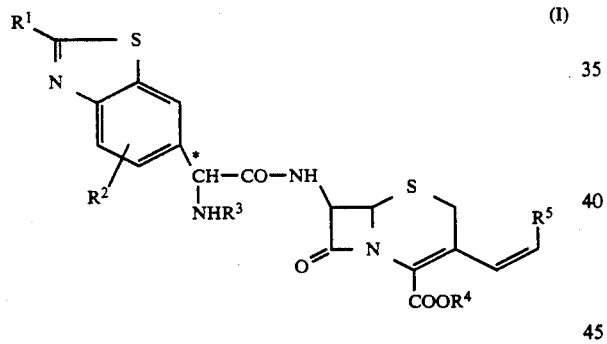

in which $R^1$ represents hydrogen, or represents a straight-chain, branched or cyclic alkyl or alkenyl radical which has up to 10 carbon atoms and can be substituted by halogen, hydroxyl, alkoxy with up to 6 carbon atoms, cyano, carboxyl, optionally substituted aryl, alkylsulphonyl with up to 6 carbon atoms or sulpho, or by a group of the formula

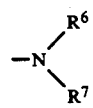

wherein $R^6$ and $R^7$ are identical or different and denote hydrogen, alkyl with up to 8 carbon atoms, aryl with 6 to 12 carbon atoms, aralkyl with 7 to 14 carbon atoms or acyl with up to 7 carbon atoms, or an-amino-protective group, or $R^1$ represents aryl which has 6 to 12 carbon atoms and can be substituted by halogen, cyano, nitro, alkyl, alkoxy or alkylthio with in each case up to 6 carbon atoms, trifluoromethyl or trifluoromethoxy, or represents halogen, alkoxy, alkylthio or alkylsulphonyl with in each case up to 8 carbon atoms, mercapto, hydroxyl, phenylthio, phenyloxy, benzylthio, benzyloxy, sulpho, sulphamoyl, —PO(OH)₂, —NHNH₂, —N-HOH, guanidino, amidino, heterocyclyl, heterocyclylthio or heterocyclyloxy, with heterocyclic radicals from the series comprising pyrrolyl, pyrrolidinyl, pyrazolyl, imidazolyl, pyridyl, pyridazinyl, pyrimidyl, pyrazinyl, quinolyl, isoquinolyl, indolyl, quinoxazolyl, quinazolyl, piperidinyl, morpholinyl, piperazinyl, thiomorpholinyl, furyl, thienyl, oxazolyl, thiazolyl, isoxazolyl, thiadiazolyl, triazolyl and tetrazolyl, which can in turn be substituted by methyl, methoxy or halogen, or represents a group of the formula

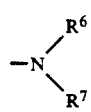

wherein $R^6$ and $R^7$ have the abovementioned meaning, $R^2$ represents hydrogen, alkyl, alkoxy or alkylthio with in each case up to 8 carbon atoms, trifluoromethyl, trifluoromethoxy, hydroxyl, mercapto, nitro, cyano, halogen or amino, $R^3$ represents hydrogen, or represents an amino-protective group, $R^4$ represents hydrogen, or represents a carboxyl-protective group, or represents an ester which can be split off in vivo and $R^5$ represents hydrogen, or represents straight-chain or branched alkyl which has up to 6 carbon atoms and can be substituted by halogen alkoxy or alkylthio with in each case up to 6 carbon atoms, hydroxyl or amino, or by a radical of the formula

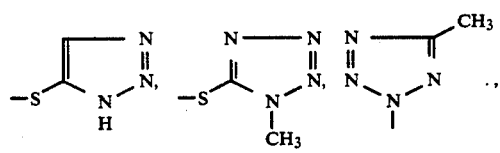

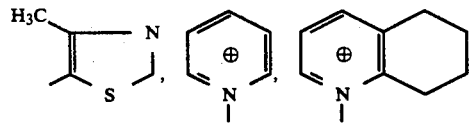

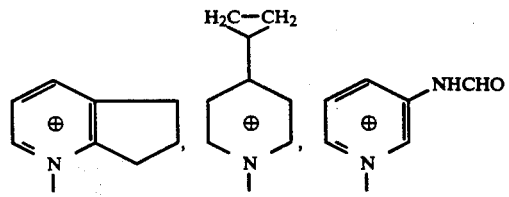

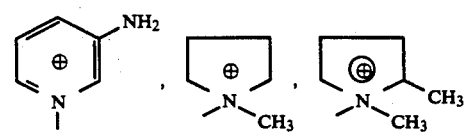

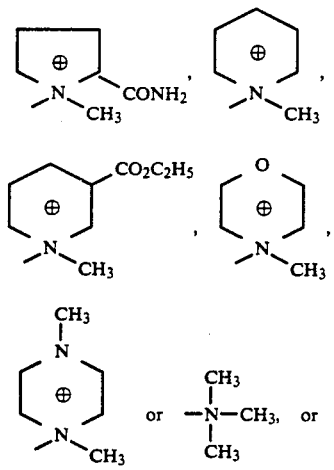

$R^5$ represents halogen, cyano, trifluoromethyl, carboxyl, alkoxycarbonyl with up to 8 carbon atoms, alkylsulphonyl or alkylsulphonyloxy with in each case up to 8 carbon atoms, phenylsulphonyl, tolylsulphonyl, phenylsulphonyloxy, tolylsulphonyloxy, sulphamoyl or dialkylsulphamoyl with in each case up to 6 carbon atoms per alkyl group, or represents cycloalkyl which has 3 to 8 carbon atoms and can be substituted by alkyl, alkoxy or alkoxycarbonyl with in each case up to 6 carbon atoms, carboxyl, carbamoyl, halogen, cyano or phenyl, or represents cycloalkylalkyl with 3 to 6 ring members and 4 to 10 carbon atoms, or represents straight-chain or branched alkinyl which has up to 8 carbon atoms and can be substituted by aryl with 6 to 12 carbon atoms, carboxyl or alkoxycarbonyl with up to 8 carbon atoms, or by halogen, or represents aryl which has 6 to 12 carbon atoms and can be substituted by halogen, cyano, nitro, trifluoromethyl, trifluoromethoxy, trifluoromethylthio or alkyl, alkoxy or alkylthio with in each case up to 6 carbon atoms, or represents a heterocyclic radical from the series comprising thienyl, furyl, pyridyl, pyridyl oxide, pyrimidyl, pyrazinyl, pyridazinyl, pyrazolyl, imidazolyl, triazolyl, tetrazolyl, oxazolyl, thiazolyl or thiadiazolyl, it being possible for the heterocyclic radicals to be substituted by alkyl or alkoxy with in each case up to 6 carbon atoms, halogen, nitro or cyano, or represents a group of the formula $-NR^8R^9$, $-CH_2-R^{10}$ or $-S-R^{11}$, wherein $R^8$ and $R^9$ are identical or different and denote hydrogen, alkyl with up to 6 carbon atoms, aryl with 6 to 12 carbon atoms, aralkyl with 7 to 14 carbon atoms, acyl with up to 7 carbon atoms or an amino-protective group, or wherein $R^8$ and $R^9$, together with the nitrogen atom, form a 5- to 7-membered ring, which can be interrupted by O, S, NH, N-alkyl with up to 4 carbon atoms or N-phenyl, $R^{10}$ denotes a heterocyclic radical from the series comprising thienyl, furyl, pyridyl, pyridyl oxide, pyrimidyl, pyrazinyl, pyridazinyl, pyrazolyl, imidazolyl, triazolyl, tetrazolyl, oxazolyl, thiazolyl or thiadiazolyl, it being possible for the heterocyclic radicals to be substituted by alkyl, alkoxy or alkylthio with in each case up to 6 carbon atoms, halogen, nitro, cyano, trifluoromethyl or trifluoromethoxy, and $R^{11}$ denotes a heterocyclic radical from the series comprising thienyl, furyl, pyridyl, pyridyl oxide, pyrimidyl, imidazolyl, triazolyl, oxazolyl and thiadiazolyl, it being possible for the heterocyclic radicals to be substituted by alkyl or alkoxy with in each case up to 6 carbon atoms, halogen, trifluoromethyl, trifluoromethoxy, nitro or cyano, and salts thereof.

An amino-protective group in the context of the definition given above in general represents a protective group customary in β-lactam chemistry from the series comprising benzyl, tert.-butoxycarbonyl, benzyloxycarbonyl, 2-nitrobenzyloxycarbonyl, 4-nitrobenzyloxycarbonyl, 2,2,2-trichloro-ethoxycarbonyl, fluorenyl-(9)-methoxycarbonyl, N-diphenyl-methoxycarbonyl, acetoacetyl, 2-nitrobenzoyl, 2-nitrophenylsulfenyl, phthaloyl, triyl, vinyloxycarbonyl, formyl, benzoyl, allyloxycarbonyl, 2,4-dimethoxybenzyloxycarbonyl, 2-methylthio-ethoxycarbonyl, 1,3-dithian-2-ylmethoxycarbonyl (Dmox), trimethyl-, triethyl-, triphenylsilyl, tert.-butyl-dimethylsilyl, tert.-butyldiphenylsilyl, 1-methyl-2-benzoyl-vinyl, 1-methyl-2-ethoxycarbonyl-vinyl, 1-methyl-2-methoxycarbonyl-vinyl, 1-methyl-2-(2,6-dimethoxybenzoyl)vinyl, 4-methoxy-benzyloxycarbonyl 4-methoxyphenyl, 4-methoxymethyloxy-phenyl, 4-[2-methoxyethoxy)methyloxy]phenyl, 3,4-dimethoxyphenyl, benzyl, 4-nitrobenzyl, 4-methoxybenzyl, 2,4-dimethoxybenzyl, 3,4-dimethoxybenzyl, 2,4,6-trimethoxybenzyl, acetyl, chloroacetyl, trichloroacetyl, trifluoroacetyl, methoxycarbonyl, allyloxycarbonyl, methoxycarbonylmethyl, tert.-butoxycarbonylmethyl, allyloxymethyl, bis-(4-methoxy phenyl)methyl, methoxymethyl, methylghiomethyl, methoxyethoxymethyl, 2-(methylthiomethoxy)ethoxycarbonyl, 2-hydroxy-2-phenylmethyl, methoxy-(4-methoxyphenyl)methyl, [2-(trimethylsilyl)ethoxy]methyl, 1-methyl-2-ethoxy- or -2-methoxyvinyl, mesyl and ethylsulphonyl (see E. Wünsch, Methods of Organic Chemistry, Houben-Weyl, Vol. 15/I (1074).

A carboxyl-protective group in the context of the definition given above represents the carboxyl-protective groups customary in β-lactam chemistry. Groups which can easily be split off may be mentioned as preferred, such as, for example: methyl, ethyl, tert.-butyl, decyl, 2-chloroethyl, 2,2,2-trichloroethyl, cyanoethyl, diphenylmethyl, triphenylmethyl, acetoxymethyl, allyl, benzyl, 4-methoxyphenyl, 4-nitrobenzyl, 2-nitrobenzyl, 4-methoxybenzyl, 2,4-dimethoxybenzyl, trimethylsilylethyl, trimethylsilyl, tert.-butyl-dimethylsilyl, acetonyl, 1-phenoxyethyl or 2-methyl-2-propenyl. (see a) E. Wünsch, Methods of Organic Chemistry, Houben-Weyl, Vol. 15/I (1974) and b) Th. W. Greene, Protective Groups in Organic Synthesis, J. Wiley & Sons (1981)).

If $R^4$ represents an ester radical which can easily be split off in vivo, by these are meant pharmaceutically tolerated ester radicals which are easily hydrolyzed in vivo to give free carboxyl groups ($R^4$=H).

Such ester radicals are well-known in the β-lactam field. In most cases, they improve the absorption properties of the β-lactam compounds. The radical $R^4$ should furthermore be such that it imparts pharmaceutically acceptable properties to a compound of the formula (I) and liberates pharmaceutically acceptable fragments when split in vivo.

Examples of such groups are to be found in DE-OS (German Published Specifications) 2 228 255 and 2 350 230. Preferred ester groups which can be split off in vivo are those of the following formulae:

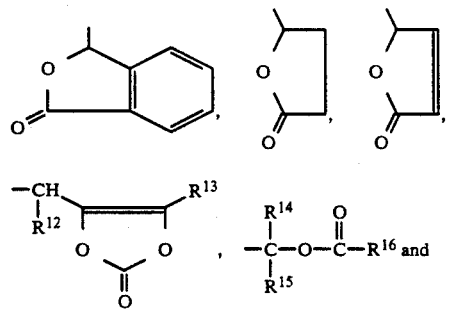

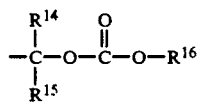

wherein
R¹² and R¹³ are identical or different and represent hydrogen or phenyl, or represent $C_1$–$C_4$-alkyl, preferably methyl,
R¹⁴ and R¹⁵ are identical or different and represent hydrogen, or represent $C_1$–$C_4$-alkyl, preferably methyl, and
R¹⁶ represents $C_1$–$C_6$-alkyl, preferably $C_1$–$C_4$-alkyl.

The compounds of the general formula (I) according to the invention can be in the form of the free acids, esters, inner salts

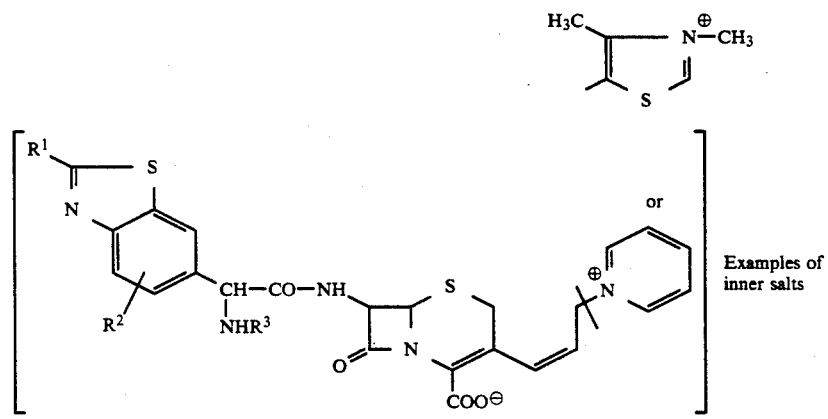

Examples of inner salts or non-toxic physiologically tolerated salts with a counter-cation

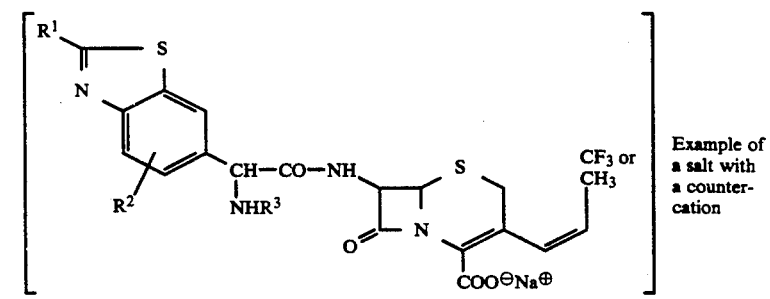

Example of a salt with a counter-cation or, if R⁴ is a positively charged radical, non-toxic physiologically tolerated salts with a counter-anion.

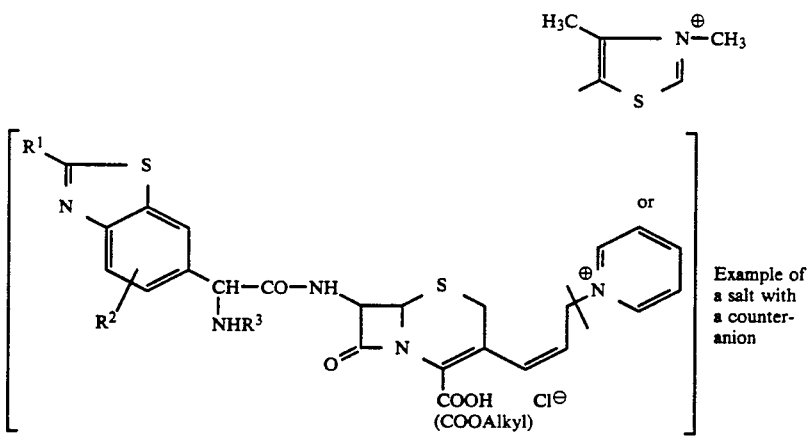

Preferred counter-cations which may be mentioned are alkali metal or alkaline earth metal cations, such as, for example, sodium, potassium, magnesium or calcium ions, or aluminum or ammonium ions, and non-toxic substituted ammonium ions of amines such as di-lower alkylamines, tri-lower alkylamines, procaine, dibenzylamine, N,N'-dibenzylethylenediamine, N-benzyl-β-phenyl-ethylamine, N-methylmorpholine, 1-ephenamine, dihydroabietylamine, N,N'-bis-dihydroabietylethylenediamine, N-lower alkylpiperidines or other amines which can be used to form salts of β-lactam compounds.

Preferred counter-anions which may be mentioned are inorganic or organic acid radicals, such as, for example, chloride, bromide, iodide, sulphate, hydrogen sulphate, phosphate, hydrogen phosphate, carbonate or bicarbonate, or sulphonates, such as methanesulphonate, ethanesulphonate, toluenesulphonate, benzenesulphonate or naphthalenedisulphonate, or carboxylates, such as acetate, formate, oxalate, tartrate, citrate, maleate, fumarate, benzoate, succinate and lactate.

The compounds of the general formula (I) exist (in respect of the double bond) in the Z-(cis) and in the E-(trans) configuration. The compounds with the Z-(cis) configuration are preferred. Because of the presence of the asymmetric carbon atom labelled with * (see formula I), the β-lactam antibiotics of the general formula (I) according to the invention include the D-, L- and D,L-forms. Both the diastereomer mixtures and the D-form and L-form of the compounds according to the invention can be used for the treatment of bacterial infection diseases. The D-forms of the compounds according to the invention are particularly preferred.

Compounds of the general formula (I) which may be mentioned as preferred are those in which $R^1$ represents hydrogen, or represents straight-chain, branched or cyclic alkyl with up to 6 carbon atoms which can be substituted by flourine, chlorine, bromine, hydroxyl, alkoxy or alkoxycarbonyl with in each case up to 4 carbon atoms, cyano or phenyl, or by a group of the formula $-NR^6R^7$, wherein $R^6$ and $R^7$ are identical or different and represent hydrogen, alkyl with up to 6 carbon atoms, phenyl, benzyl or an amino-protective group from the series comprising 4-methoxyphenyl, 3,4-dimethoxyphenyl, 4-methoxymethyl oxyphenyl, 4-[(2-methoxyethoxy)methoxy]phenyl, benzyl, 4-methoxybenzyl, 2,4-dimethoxybenzyl, 3,4-dimethoxybenzyl, 2,4,6-trimethoxybenzyl, methoxy-(4-methoxyphenyl)methyl, trimethylsilyl, triethylsilyl, tert.-butyl-dimethylsilyl, tert.-butyl-diphenylsilyl, methoxycarbonylmethyl, tert.-butoxycarbonylmethyl and 2-hydroxy-2-phenylethyl, or $R^1$ represents phenyl which is optionally substituted by fluorine, chlorine, bromine, alkyl or alkoxy with up to 6 carbon atoms, trifluoromethyl, trifluoromethoxy or cyano, or represents fluorine, chlorine, bromine, alkoxy, alkylthio or alkylsulphonyl with in each case up to 6 carbon atoms, mercapto, hydroxyl, phenylthio, phenyloxy or sulphamoyl, or represents a group of the formula $-NR^6R^7$, $R^2$ represents hydrogen, methyl, methoxy, trifluoromethyl, trifluoromethoxy, nitro, cyano, fluorine, chlorine, bromine or hydroxyl, $R^3$ represents hydrogen, or represents an amino-protective group from the series comprising: tert.-butoxycarbonyl, benzyloxycarbonyl, 2.2.2-trichloroethoxycarbonyl, trityl, vinyloxycarbonyl, allyloxycarbonyl, 2.4-dimethoxybenzyloxycarbonyl, 1-methyl-2-benzoyl-vinyl, 1-methyl-2-ethoxycarbonyl-vinyl, 1-methyl-2-methoxy-carbonyl-vinyl, 4-methoxyphenyl, 3,4-dimethoxyphenyl, 4-methoxymethoxyphenyl, 4-[(2-methoxyethoxy)methoxy]phenyl, benzyl, 4-methoxybenzyl, 2,4-dimethoxybenzyl, 3,4-dimethoxybenzyl, 2,4,6-trimethoxybenzyl, methoxy-(4-methoxyphenyl)methyl, trimethylsilyl, triethylsilyl, tert.-butyl-dimethylsilyl, tert.-butyl-diphenylsilyl, methoxycarbonylmethyl, tert.-butoxycarbonylmethyl, 2-hydroxy-2-phenylethyl, tert.-butoxycarbonyl, 1-methyl-2-benzoyl-vinyl and 1-methyl-2-methoxy-vinyl, $R^4$ represents hydrogen, or represents methyl, ethyl, tert.-butyl, 2-chloroethyl, 2,2,2-trichloroethyl, cyanoethyl, diphenylmethyl, triphenylmethyl, acetoxymethyl, allyl, benzyl, 4-methoxybenzyl, 2,4-dimethoxybenzyl, 1-phenoxyethyl, 2-methyl-2-propenyl, 4-nitrobenzyl, 2-nitrobenzyl, trimethylsilylethyl or tert.-butyldimethylsilylethyl, or represents a radical of the formula

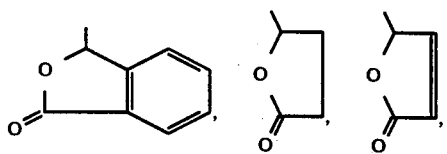

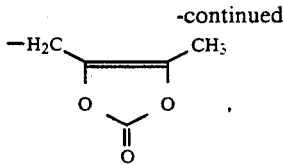

—CH₂—OCO—C(CH₃)₃,

—CH(CH₃)—OCOOC₂H₅ or

—CH₂—OCOCH₃ and R⁵ represents hydrogen, or represents straight-chain or branched alkyl which has up to 4 carbon atoms and can be substituted by fluorine, chlorine, bromine, iodine, alkoxy with up to 3 carbon atoms, hydroxyl or amino, or by a radical of the formula

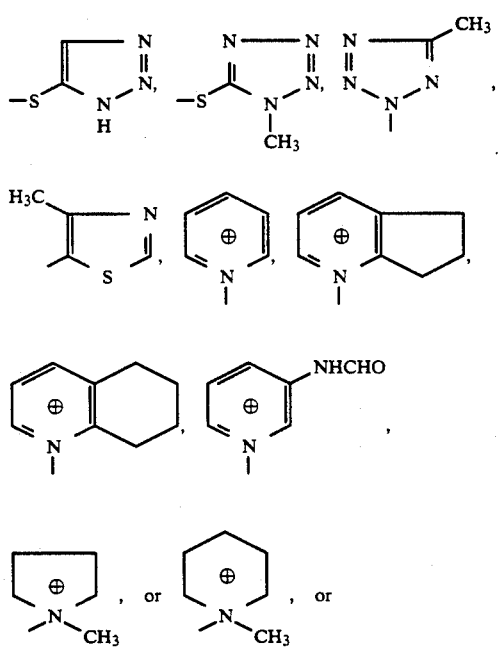

R⁵ represents fluorine, chlorine, bromine, cyano, trifluoromethyl, carboxyl, alkoxycarbonyl with up to 6 carbon atoms, alkylsulphonyl or alkylsulphonyloxy with in each case up to 6 carbon atoms, phenylsulphonyl, tolylsulphonyl, phenylsulphonyloxy or tolylsulphonyloxy, or represents cyclopropyl, cyclopentyl or cyclohexyl, which can be substituted by alkyl, alkoxy or alkoxycarbonyl with in each case up to 4 carbon atoms, fluorine, chlorine, bromine or phenyl, or represents cyclopropylmethyl, cyclopentylmethyl or cyclohexylmethyl, or represents straight-chain or branched alkinyl which has up to 6 carbon atoms and can be substituted by phenyl, carboxyl or alkoxycarbonyl with up to 6 carbon atoms, or by fluorine, chlorine or bromine, or represents phenyl, which can be substituted by fluorine, chlorine, bromine, cyano, nitro, trifluoromethyl, trifluoromethoxy or alkyl or alkoxy with up to 4 carbon atoms, or represents a heterocyclic radical from the series comprising thienyl, furyl, pyridyl, pyridyl oxide, pyrimidyl, pyrazolyl, triazolyl, tetrazolyl, oxazolyl, thiazolyl and thiadiazolyl, it being possible for the heterocyclic radicals to be substituted by alkyl or alkoxy with in each case up to 4 carbon atoms, fluorine, chlorine, bromine or nitro, or represents a group of the formula —NR⁸R⁹, —CH₂—R¹⁰ or —S—R¹¹, wherein R⁸ and R⁹ are identical or different and denote. hydrogen, alkyl with up to 4 carbon atoms, phenyl, benzyl or an amino-protective group from the series comprising 4-methoxyphenyl, 3,4-dimethoxyphenyl, 4-methoxymethoxyphenyl, 4-[(2-methoxyethoxy)methoxy]phenyl, benzyl, 4-methoxybenzyl, 2,4-dimethoxybenzyl, 3,4-dimethoxybenzyl, 2,4,6-trimethoxybenzyl, methoxy-(4-methoxyphenyl)methyl, trimethylsilyl, triethylsilyl, tert.-butyl-dimethylsilyl, tert.-butyl-diphenylsilyl, methoxycarbonyl-methyl, tert.-butoxycarbonylmethyl and 2-hydroxy-2-phenylethyl, or wherein R⁸ and R⁹, together with the nitrogen atom, form a pyrrolidine, piperidine, morpholine, thiomorpholine, piperazine or 4-methyl- or 4-phenylpiperazine ring, R¹⁰ denotes a heterocyclic ring from the series comprising thienyl, furyl, pyridyl, pyridyl oxide, pyrimidyl, pyrazolyl, triazolyl, tetrazolyl, oxazolyl, thiazolyl and thiadiazolyl, it being possible for the heterocyclic radicals to be substituted by alkyl or alkoxy with in each case up to 4 carbon atoms, fluorine, chlorine, bromine or nitro, and R¹¹ denotes a heterocyclic ring from the series comprising thienyl, furyl, pyridyl, pyridyl oxide, pyrimidyl, pyrazolyl, triazolyl, oxazolyl and thiadiazolyl, it being possible for the heterocyclic radicals to be substituted by alkyl or alkoxy with in each case up to 4 carbon atoms, fluorine, chlorine, bromine or nitro, and salts thereof.

Compounds of the general formula (I) which may be mentioned as particularly preferred are those in which R¹ represents hydrogen, or represents straight-chain or branched alkyl with up to 4 carbon atoms, or represents a group of the formula —NHR⁶ wherein R⁶ denotes hydrogen, methyl, ethyl, propyl or isopropyl, R² represents hydrogen or hydroxyl, R³ represents hydrogen, or represents benzyloxycarbonyl, 1-methyl-2-benzoyl-vinyl-, 4-methoxybenzyloxycarbonyl, 2-nitrophenylsulfenyl (NPS), trityl, allyloxycarbonyl, tert.-butyl-dimethylsilyl, 1-methyl-2-methoxycarbonyl-vinyl (MMV) or tert.-butoxycarbonyl (Boc), R⁴ represents hydrogen, or represents methyl, ethyl, tert.-butyl, diphenylmethyl, 2,2,2-trichloroethyl, allyl, acetoxymethyl, 4-nitrobenzyl, 2-nitrobenzyl, 4-methoxybenzyl, benzyl or trimethylsilylethyl, or represents a radical of the formula

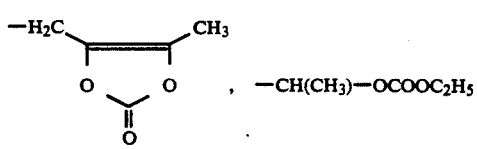

or —CH₂—OCO—C(CH₃)₃, and

R⁵ represents hydrogen, methyl, chloromethyl, dihydroxyethyl or iodomethyl, or represents a radical of the formula

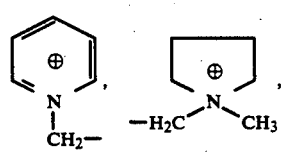

-continued

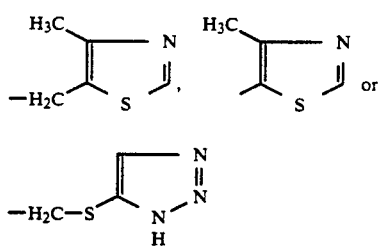

and salts thereof.

Other particularly preferred compounds are those in which $R^1$ represents hydrogen, or represents straight-chain or branched alkyl or cyclic, saturated or unsaturated alkyl (cycloalkyl, alkenyl or alkinyl) which has up to 6 carbon atoms and can be substituted by fluorine, chlorine, methoxy, cyano, phenyl, dimethylamino, hydroxyl or diethylamino, or represents phenyl, which can be substituted by fluorine, chlorine, methyl, methoxy, trifluoromethyl, amino or trifluoromethoxy, or represents chlorine, alkoxy or alkylsulphonyl with in each case up to 4 carbon atoms, mercapto, hydroxyl, $SO_3H$, $SO_2NH_2$, guanidino, $NH-NH_2$ or $NH-OH$, or represents a group of the formula $-NHR^6$, wherein $R^6$ denotes hydrogen, alkyl with up to 4 carbon atoms, phenyl, benzyl or an amino-protective group from the series comprising 4-methoxyphenyl, 4-methoxybenzyl, 2,4-dimethoxybenzyl, 3,4-dimethoxybenzyl and tert.-butyl-dimethylsilyl, or $R^1$ represents optionally substituted heterocyclyl, $R^2$ represents hydrogen, or hydroxyl or methoxy, $R^3$ represents hydrogen, or represents 4-methoxyphenyl, 4-methoxybenzyl, 2,4-dimethoxybenzyl, 3,4-dimethoxybenzyl, tert.-butyl-dimethylsilyl, 1-methyl-2-methoxy-vinyl (MMV), tert.-butoxycarbonyl (Boc), benzyloxycarbonyl, trityl, alkyloxycarbonyl, 1-methyl-2-benzoylvinyl, 1-methyl-2-methoxycarbonylvinyl, 2-nitro-phenyl-sulphonyl or $R^4$ represents hydrogen, or represents methyl, ethyl, tert.-butyl, diphenylmethyl, 2,2,2-trichloroethyl, allyl, acetoxymethyl, 4-nitrobenzyl, 2-nitrobenzyl, 4-methoxybenzyl, benzyl or trimethylsilylethyl, or represents a radical of the formula

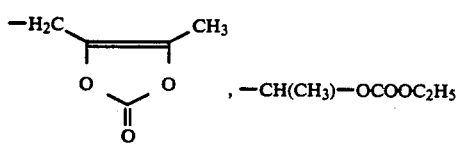

$R^5$ represents hydrogen, methyl, ethyl, dihydroxyethyl, methoxymethyl, chloromethyl or iodomethyl, chlorine, bromine trifluoromethyl, carboxyl, alkoxycarbonyl or alkylsulphonyloxy with in each case up to 4 carbon atoms, phenylsulphonyloxy, tolylsulphonyloxy, cyclopropyl, cyclopentyl, cyclohexyl, cyclopropylmethyl or cyclopentylmethyl, or represents alkinyl which has up to 4 carbon atoms and can be substituted by phenyl, carboxyl or alkoxycarbonyl with up to 4 carbon atoms, or represents phenyl, or represents a radical of the formula

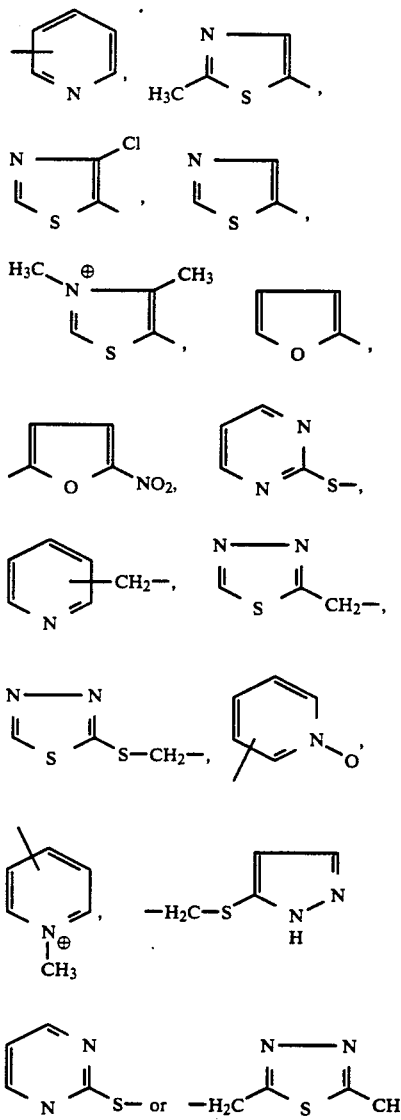

and salts thereof.

The compounds listed in the following table are moreover especially preferred:

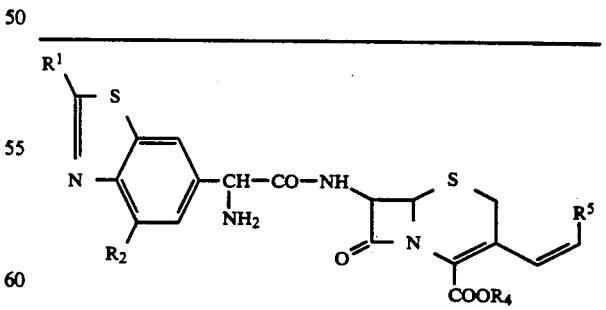

| $R^1$ | $R^2$ | $R^4$ | $R^5$ |
|---|---|---|---|
| $H_3C-$ | H | H | $-CH_3$ |
| $H_2N-$ | H | H | $-C_2H_5$ |
| $H_2N-$ | H | H | $-CH_2Cl$ |
| $H_2N-$ | H | H | $-CH_2-OCH_3$ |
| $H_2N-$ | H | H | $-CH_2I$ |

-continued

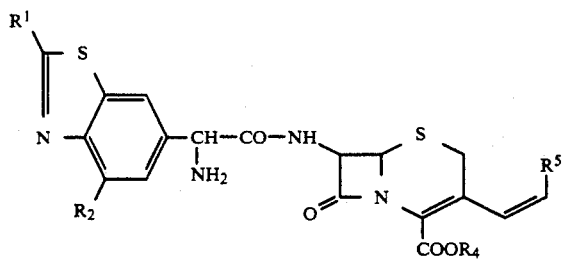

| R¹ | R² | R⁴ | R⁵ |
|---|---|---|---|

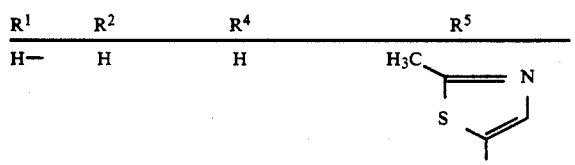

| $H_2N$ | H | H | $-H_2C-S-\underset{\underset{H}{N}}{\overset{N=N}{\vert\vert}}$ (triazolylmethylthio) |
| $H_2N$ | H | $CH_2OCOCH_3$ | $CH_3$ |
| $H_2N$ | OH | H | $CH_3$ |
| $H_2N$ | H | $-CH_2OCOCH_3$ | $CH_2-OCH_3$ |
| H | $H_2N$ | H | $CH_3$ |
| $H_2N$ | Cl | H | $CH_3$ |
| $H_2N$ | H | $-CH_2OCOC(CH_3)_3$ | (thiazolyl-CH₃) |
| H | OH | H | $CH_3$ |
| $H_2N$ | H | H | $-CH(OH)CH_2OH$ |
| ▷ | H | H | $CF_3$ |
| $CH_3$ | $H_2N$ | H | (methylthiazolyl) |
| $H_2N$ | OH | $-CH(CH_3)OCOOC_2H_5$ | $CH_3$ |
| $H_2N$ | H | H | cyclopropyl-$CH_2-$ |
| $H_2N$ | H | H | $CH_3-C\equiv C-$ |
| $CH_3$ | H | $CH_2-OCOC(CH_3)_3$ | $CF_3-$ |
| $H_2N-$ | H | H | Ph-$C\equiv C-$ |

-continued

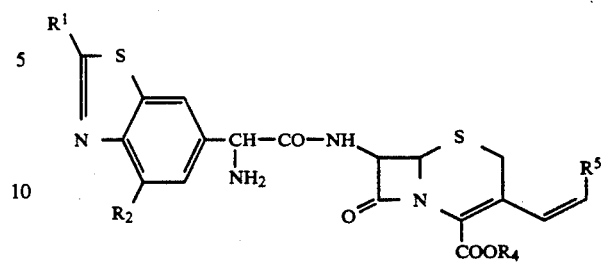

| R¹ | R² | R⁴ | R⁵ |
|---|---|---|---|
| $H_2N-$ | OH | $CH_2OCOCH_3$ | (thiazolyl) |
| $H_2N-$ | OH | H | $-N(CH_3)_2$ |
| $H_2N-$ | H | H | (pyridyl) |
| ▷ | H | H | $CF_3$ |
| $H_2N$ | H | H | Cl |
| $H_2N$ | H | H | $CH_2Cl$ |
| $H_2N$ | H | H | (imidazolyl) |
| $H_2N$ | H | H | $-CH_2-S-\underset{\underset{H}{N}}{\overset{N}{\vert\vert}}$ (pyrazolylmethylthio) |
| $H_2N$ | $O_2N$ | H | Ph |
| $H_2N$ | HO— | H | (furyl) |

A process has furthermore been found for the preparation of the substituted vinylcephalosporin compounds of the general formula (I) according to the invention, which is characterized in that [A] substituted cephalosporin compounds of the general formula (II)

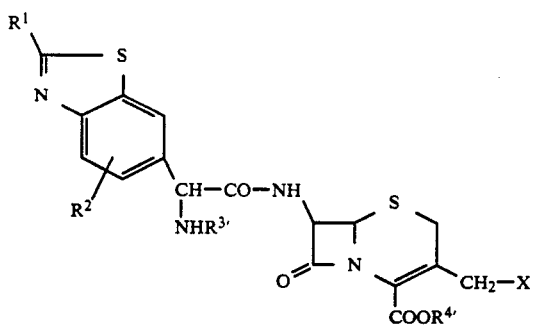

(II)

in which
R$^1$ and R$^2$ have the abovementioned meaning,
R$^{3'}$ represents an amino-protective group,
R$^{4'}$ represents a carboxyl-protective group and
X represents a group of the formula

wherein
R$^{17}$ and R$^{18}$ are identical or different and denote alkyl, phenyl or tolyl and
Z$^-$ denotes a halide anion, preferably chloride, bromide or iodide,
are reacted with aldehydes of the general formula (III)

$$R^5\text{—CHO} \qquad (III)$$

in which
R$^5$ has the abovementioned meaning, in inert solvents in the presence of bases, or in that [B] phosphonium compounds of the general formula (IV)

$$R^5\text{—CH}_2\text{—X} \qquad (IV)$$

in which
R$^5$ has the abovementioned meaning and
X represents a group of the formula

wherein
R$^{17}$ and R$^{18}$ are identical or different and denote alkyl, phenyl or tolyl and
Z$^-$ denotes a halide anion, preferably chloride, bromide or iodide, are reacted with cephalosporinaldehydes of the general formula (V)

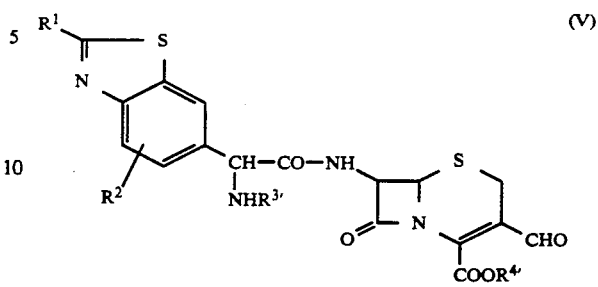

(V)

in which
R$^1$ and R$^2$ have the abovementioned meaning,
R$^{3'}$ represents an amino-protective group and
R$^{4'}$ represents a carboxyl-protective group, in inert solvents in the presence of bases, or in that [C] carboxylic acids of the general formula (VI)

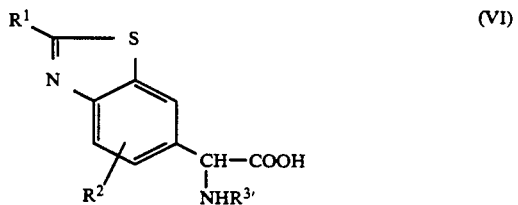

(VI)

in which
R$^1$ and R$^2$ have the abovementioned meaning and
R$^{3'}$ represents an amino-protective group, after activation of the carboxyl group by conversion into a mixed anhydride, for example with ethyl chloroformate, isobutyl chloroformate or methanesulphonyl chloride, or by conversion into the acid halide, or by conversion into an activated ester, for example with N-hydroxybenzotriazole and dicyclohexylcarbodiimide (DCC), are reacted with the vinylcephalosporinamines of the general formula (VII)

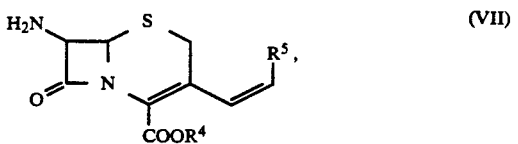

(VII)

in which
R$^4$ and R$^5$ have the abovementioned meaning, and, if appropriate, protective groups are then split off and the desired salts are prepared or the free acids are prepared from the salts.

The process according to the invention can be illustrated by the following equation:

Process variant A:

-continued
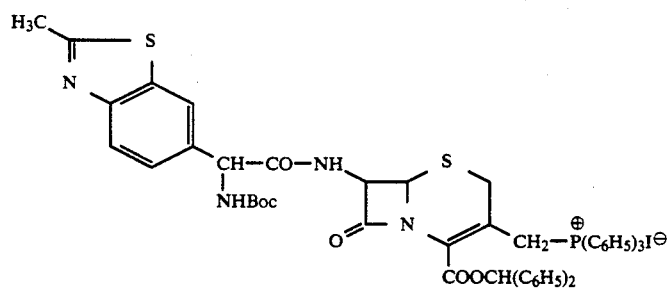
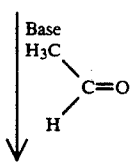
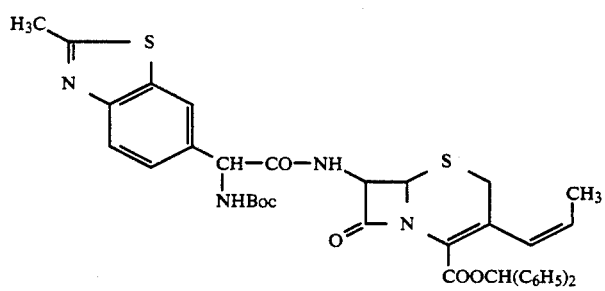
Process variant B:
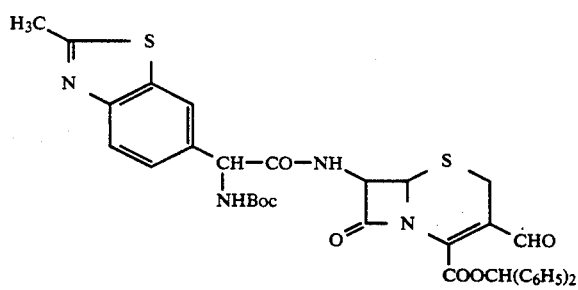
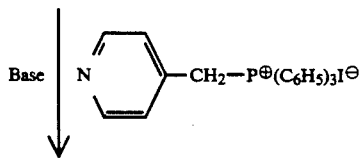
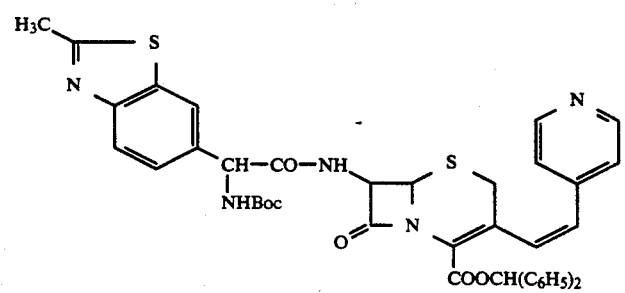
Process variant C -continued

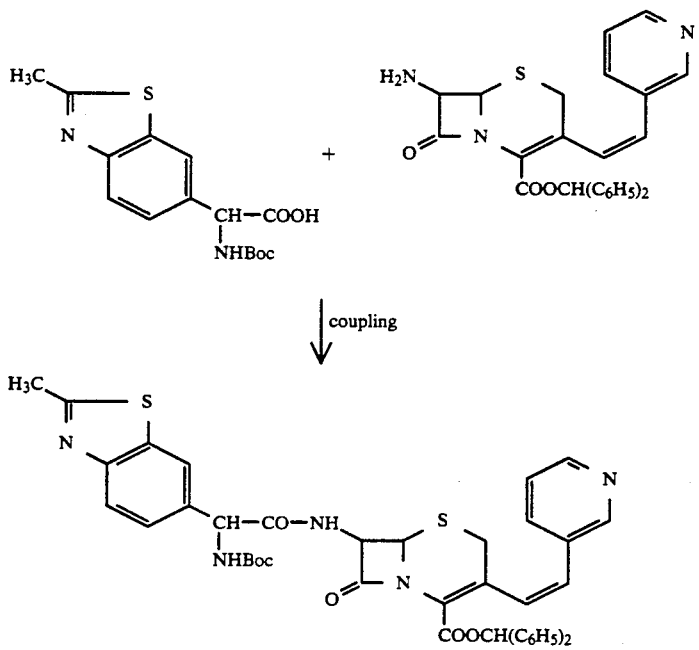

* Boc = (H₃C)₃C—O—CO—

Process variants A and B

Suitable inert solvents for process variants A and B are the customary organic solvents which do not change under the reaction conditions. These include, preferably, ethers, such as diethyl ether, butyl methyl ether, dioxane or tetrahydrofuran, or hydrocarbons, such as benzene, toluene, xylene or cyclohexane, or amides, such as dimethylformamide or hexamethylphosphoric acid triamide, or alcohols, such as methanol, ethanol, propanol or isopropanol, or chlorohydrocarbons, such as methylene chloride, chloroform or carbon tetrachloride, or acetone, acetonitrile or ethyl acetate. It is also possible to use mixtures of the solvents mentioned.

Suitable bases for process variants A and B are the customary basic compounds. These include, preferably, alkali metal or alkaline earth metal hydroxides, such as, for example, sodium hydroxide, potassium hydroxide or barium hydroxide, or alkali metal carbonates, such as sodium carbonate, sodium bicarbonate or potassium carbonate, or alkali metal alcoholates, such as sodium methanolate, sodium ethanolate, potassium methanolate, potassium ethanolate or potassium tert.-butylate.

The choice of solvent and base depends on the stability, hydrolysis-sensitivity and CH-acidity of the corresponding phosphorus compound. Solvents which are particularly preferably used are chlorohydrocarbons, such as, for example, methylene chloride, chloroform or carbon tetrachloride, in the presence of dimethylformamide as a co-solvent. Bases which are particularly preferably used are alkali metal carbonates, such as sodium carbonate, sodium bicarbonate or potassium carbonate, or alkali metal or alkaline earth metal hydroxides, such as, for example, sodium hydroxide, potassium hydroxide or barium hydroxide, particularly preferably in the form of their aqueous solutions.

The reaction is in general carried out in a temperature range from −30° C. to +80° C., preferably from 0° C. to +30° C.

The reaction can be carried out under normal, increased or reduced pressure (for example in a range from 0.5 to 5 bar). It is in general carried out under normal pressure.

In carrying out process variants A and B, the phosphorus compound (II) or (IV) is in general employed in an amount of 1 to 3 mols, preferably in molar amounts, per mol of the aldehyde (III) or (V). The bases are in general employed in an amount of 1 to 5 mols, preferably 1 to 2 mols, per mol of the phosphorus compounds.

Process variants A and B are particularly preferably carried out as a Wittig reaction. In carrying out the process according to the invention, it is also possible, instead of the phosphonium salts [$X = -P(R^{13})_3 + Z^-$], for the corresponding phosphoranes

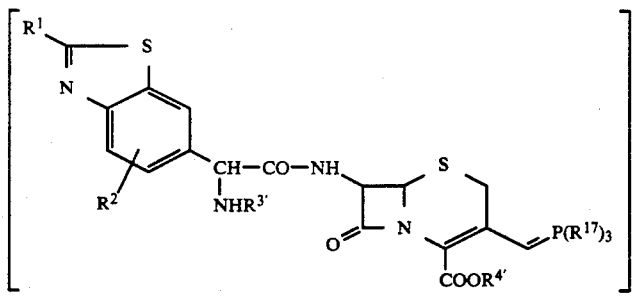

which have first been prepared from the corresponding phosphonium salts and base in a separate reaction, to be employed directly. However, it has proved to be advantageous to carry out the reaction with the triphenylphosphonium salts ($X=P^+(C_6H_5)_3Z^-$) in the presence of bases as a one-pot process. As a particular variant of a one-pot process, the reaction can also be carried out in the form of a phase transfer-catalyzed reaction, depending on the stability of the phosphorus compounds, solvents which can be used being ethers, hydrocarbons and halogenohydrocarbons and bases which can be employed being aqueous sodium hydroxide or potassium hydroxide solutions.

Alternatively, if the reaction is carried out by a procedure in which the corresponding phosphorane is isolated as an intermediate compound and is reacted with the aldehyde in a second step, it has moreover been found that the yield and the ratio of Z/E isomer of the end products of the general formula (I) are improved by adding a suitable lithium halide, such as, for example, lithium chloride, lithium bromide or lithium iodide. The reaction here is preferably carried out with 10 to 15 equivalents of lithium halide.

However, it is particularly preferable to carry out process variants A and B as a one-pot reaction without isolation of the intermediate product. The process variants according t9 the invention can be carried out, for example, by adding the base and then a corresponding aldehyde, if appropriate in a suitable solvent, to the phosphonium compounds, dissolved or suspended in a suitable solvent, and if appropriate warming the mixture. Working up is carried out in the customary manner by extraction, chromatography and/or crystallization.

Other specific process variants for the Wittig reaction are described, inter alia, in the following references: J. Fuhrhop and G. Penzlin: Organic Synthesis, Verlag Chemie, 1983, pages 26–35; R. K. Mackie and D. M. Smith: Guidebook to Organic Synthesis, Longman Group Limited, 1982, pages 93–99; H. O. House: Stereochemistry of the Wittig Reaction with stabilized ylides: J. Org. Chem. 29, 3327–3333 (1964).

Process variant C

It has proved to be advantageous to activate amino acids and then to couple them with β-lactams, which have been dissolved as salts with an amine.

Activation of carboxylic acids of the general formula (VI) with (a) sulphonic acid derivatives of the general formula (VIII) or with (b) chloroformic acid esters, preferably ethyl chloroformate, to give anhydrides of the general formula (IXa,b), as illustrated in the following equation, is particularly advantageous:

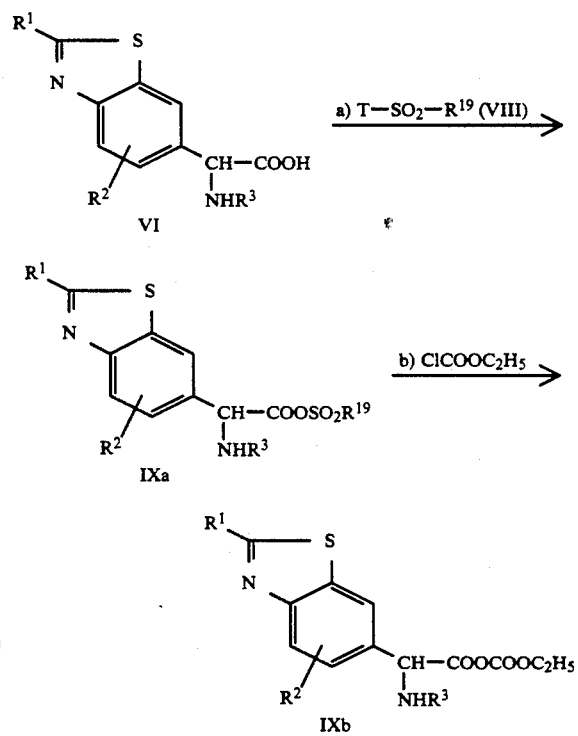

In this equation, in formula (VIII) and (IXa) T represents the radical $R^{15}$—$SO_2$—O— or halogen and $R^{19}$ represents alkyl which has up to 10 carbon atoms and is optionally substituted by fluorine, chlorine, cyano, alkyl, alkoxycarbonyl, alkoxy or alkyl with in each case up to 4 carbon atoms, or represents phenyl, which is optionally substituted by fluorine, chlorine, bromine, cyano, alkyl, alkoxy, alkylthio or alkoxycarbonyl with in each case up to 4 carbon atoms, nitro, trifluoromethyl or phenyl.

If $R^{19}$ is substituted, 1 to 3 substituents are preferably present, and those mentioned above are particularly preferably present.

$R^{19}$ especially preferably represents a methyl or p-tolyl radical.

The mixed anhydrides of the general formula (IXa,b) are prepared by dissolving the carboxylic acids of the general formula (VI) and 1 to 1.4 equivalents of an amine in a solvent and allowing the solution to react with 1 to 1.2 equivalents of a sulphonic acid derivative of the formula (VIII) or of a chloroformic acid ester.

Suitable solvents are all the solvents which do not change under the reaction conditions. These include, preferably, ethers, such as, for example, diethyl ether, dioxane or tetrahydrofuran, or chlorohydrocarbons, such as methylene chloride, chloroform or carbon tetrachloride, or amides, such as dimethylformamide or hexamethylphosphoric acid triamide, or acetonitrile or acetone. It is also possible to use mixtures of the solvents mentioned Suitable amines are tertiary amines, such as, for example, triethylamine, ethyl-diisopropylamine or tributylamine, but also sterically hindered secondary amines, such as, for example, diisopropylamine. Mixtures of the amines mentioned can also be used.

The reactions can be carried out at temperatures between $-80°$ C. and room temperature. The activation is advantageously carried out with methanesulphonyl chloride in dimethylformamide at $-40°$ C. to $-60°$ C. in the course of 0.2 to 24 hours, preferably 0.5 to 5 hours.

The solvents mentioned in the preparation of the compounds of the formula (IX) or water can be used to dissolve the vinylcephalosporinamines of the formula (VII) for the coupling with the compounds of formula (IXa) or (IXb) to obtain the compounds of formula (I), and the amines mentioned there can be used as the base.

Activation of the carboxylic acids of the general formula (VI) by conversion into an activated ester with, for example, dicyclohexylcarbodiimide, if appropriate in the presence of N-hydroxysuccinimide or 1-hydroxybenzotriazole, is also particularly advantageous.

Suitable solvents here are all the solvents which are also suitable for the preparation of anhydrides of the general formula (IXa,b) and have already been mentioned there.

The reactions can be carried out at temperatures between $-30°$ C. and $+100°$ C. Activation is advantageously carried out with 1-hydroxybenzotriazole and dicyclohexylcarbodiimide in dimethylformamide at room temperature for 2 to 6 hours, and the dicyclohexylurea which has precipitated out is then filtered off with suction and reacted with the vinylcephalosporinamines of the formula (VII) in the form of a solution of their amine salt in the course of 2 to 24 hours. The solvents mentioned for the preparation of the compounds of the formula (IX) can be used to dissolve the vinylcephalosporinamines of the formula (VII), and the amines mentioned there can be used as the base.

The aldehydes of the general formula (III) used as starting substances are known or can be prepared by known methods [Houben-Weyl's "Methoden der organischen Chemie" ("Methods of Organic Chemistry") Volume VII/1; E2].

The cephalosporin aldehydes of the general formula (V) used as starting compounds are known or can be prepared by known methods by oxidation of the corresponding 3-hydroxymethyl-cephalosporin compounds with chromium trioxide in acetone (Jones reagent), such as is described, for example, by J. A. Webber, J. L. Ott and R. T. Vasileff in J. Med. Chemistry 18, 986 (1987).

The phosphonium compounds of the general formula (IV) used as starting substances are known or can be prepared by known methods [Houben-Weyl's "Methoden der organischen Chemie" ("Methods of Organic Chemistry") Volume XII/1, 33, 167; Volume V/1b, 383, 872].

The substituted cephalosporin compounds of the general formula (II) used as starting substances are new in some cases and can be prepared by a process in which halogenomethylcephalosporin compounds of the general formula (X)

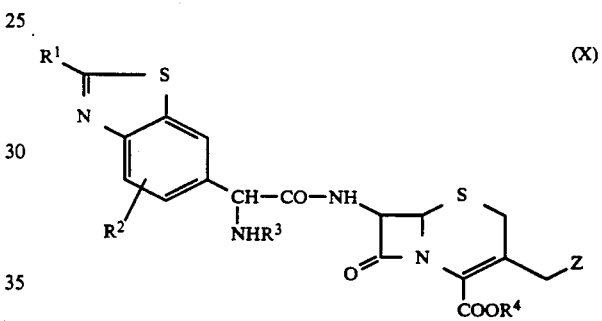

in which $R^1$, $R^2$, $R^3$ and $R^4$ have the abovementioned meaning and

Z represents halogen, preferably chlorine, bromine or iodine, are reacted with phosphorus compounds of the general formula (XI)

wherein X| represents a phosphorus compound of the formula XIa, XIb or XIc

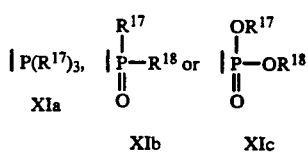

wherein $R^{17}$ and $R^{18}$ are identical or different and represent alkyl, phenyl or optionally substituted phenyl, without solvents or in inert solvents.

The process according to the invention can be illustrated by the following equation:

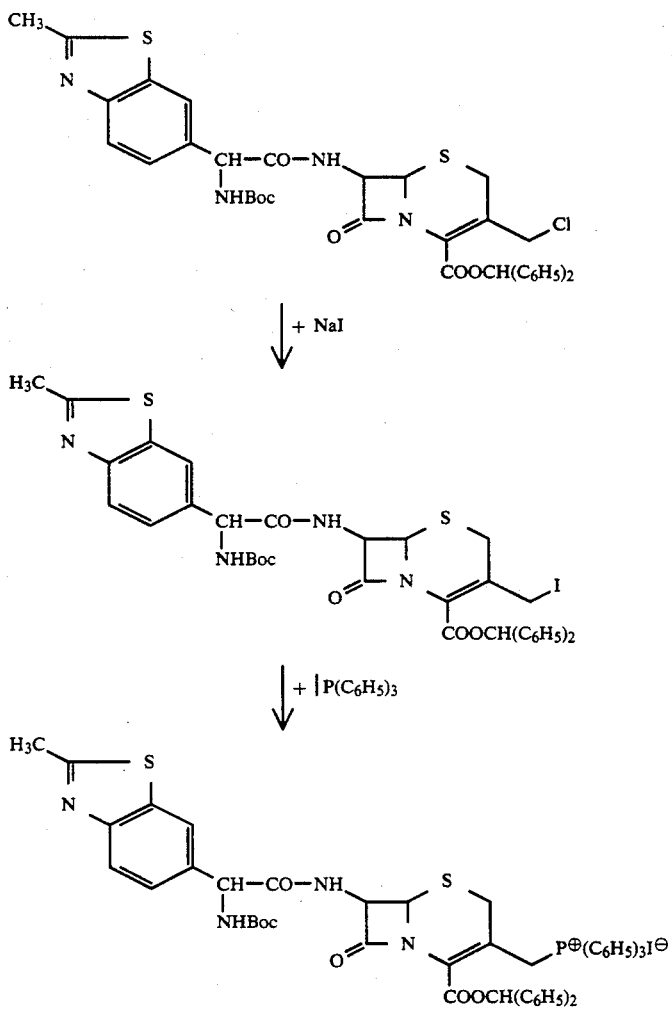

Suitable inert solvents are the customary organic solvents which are not changed under the reaction conditions. These include, preferably, ethers, such as diethyl ether, butyl methyl ether, dioxane, tetrahydrofuran or glycol dimethyl ether, or hydrocarbons, such as benzene, toluene, xylene, hexane or cyclohexane, or petroleum fractions, or halogenohydrocarbons, such as methylene chloride, chloroform, carbon tetrachloride or chlorobenzene, or ethyl acetate, acetone, dimethylformamide, hexamethylphosphoric acid triamide or dimethylacetamide. It is also possible to use mixtures of the solvents mentioned.

The reaction is in general carried out in a temperature range from 0° C. to +150° C., preferably from +20° C. to +180° C.

The reaction can be carried out under normal, increased or reduced pressure. The reaction is in general carried out under normal pressure.

The reaction is in general carried out by a procedure in which the halogenomethylcephalosporin compound and the phosphorus compound are mixed in an inert solvent and the mixture is warmed, if appropriate. The phosphorus compound is in general employed here in an amount of 1 to 5, preferably 1 to 2 mols per mol of the chloromethylcephalosporin compound.

In carrying out the process according to the invention, it has proved to be particularly advantageous to use the corresponding iodine compound (X=I) as the halogenomethylcephalosporin compound, this being obtained from the corresponding chloromethyl or bromomethyl compound by treatment with sodium iodide in dimethylformamide or acetone. It is moreover possible, if the chloromethyl or bromomethyl compounds are used, to carry out the conversion into the iodine compound and the reaction with the phosphorus compound as a one-pot reaction. For this, the corresponding bromomethyl- or chloromethylcephalosporin compounds are reacted in a suitable solvent, such as, for example, ethers, acetates, hydrocarbons or chlorohydrocarbons, but preferably acetone, with sodium iodide and the corresponding phosphorus compounds.

The halogenomethylcephalosporin compounds of the general formula (X) used as starting substances are new.

A process has been found for the preparation of the halogenomethylcephalosporins of the general formula (X), which is characterized in that carboxylic acids of the general formula (VI)

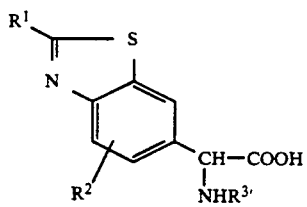

(VI)

in which

R[1] and R[2] have the meaning given and R[3'] represents an amino-protective group, after activation of the carboxyl group by conversion into a mixed anhydride, for example with ethyl chloroformate, isobutyl chloroformate or methanesulphonyl chloride, or by conversion into the acid halide, or by conversion into an activated ester with, for example, N-hydroxybenzotriazole and dicyclohexylcarbodiimide, are reacted with a β-lactam compound of the general formula (XII)

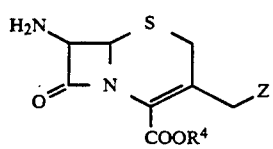

(XII)

in which

R[4] and Z have the abovementioned meaning, if appropriate, protective groups are then split off and the desired salts are prepared or the free acids are prepared from the salts.

A large number of methods known from cephalosporin or penicillin chemistry can be used for coupling carboxylic acids (VI) to the β-lactam compound (XII). It has proved to be advantageous to activate the carboxylic acids of the general formula (VI) with an amine-protective group (R₃) and then to couple them with the β-lactam compounds of the formula (XII), which have been dissolved as salts with an amine.

Activation of carboxylic acids of the general formula (VI) with (a) sulphonic acid derivatives of the general formula (VIII) or with (b) chloroformic acid esters, preferably ethyl chloroformate, to give anhydrides of the general formula (IXa, b), as illustrated in the following equation, is particularly advantageous:

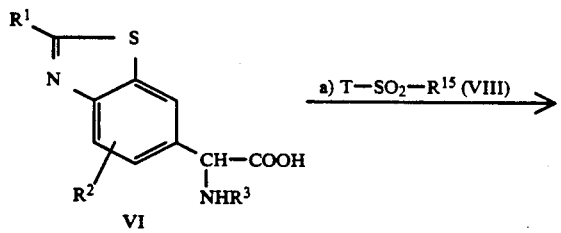

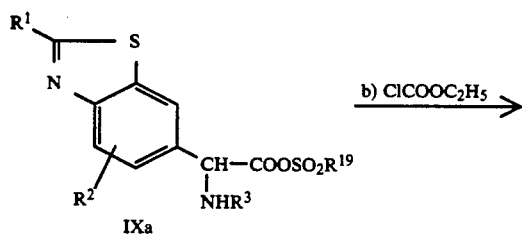

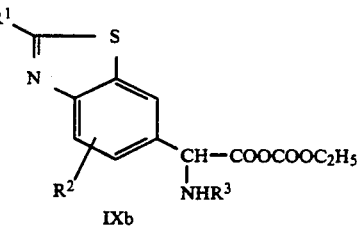

IXb

In this equation, in formula (VIII) and (IXa) T represents the radical $R^{19}$—$SO_2$—O— or halogen and $R^{19}$ represents alkyl which has up to 10 carbon atoms and is optionally substituted by fluorine, chlorine, cyano/alkyl, alkoxycarbonyl, alkoxy or alkyl with in each case up to 4 carbon atoms, or represents phenyl, which is optionally substituted by fluorine, chlorine, bromine, cyano, alkyl, alkoxy, alkylthio or alkoxycarbonyl with in each case up to 4 carbon atoms, nitro, trifluoromethyl or phenyl.

If $R^{19}$ is substituted, 1 to 3 substituents are preferably present, and those mentioned above are particularly preferably present.

$R^{19}$ especially preferably represents a methyl or p-tolyl radical.

The mixed anhydrides of the general formula (IXa,b) are prepared by dissolving the carboxylic acids of the general formula (VI) and 1 to 1.4 equivalents of an amine in a solvent and allowing the solution to react with 1 to 1.2 equivalents of a sulphonic acid derivative of the formula (VIII) or of a chloroformic acid ester.

Suitable solvents are all the solvents which do not change under the reaction conditions. These include, preferably, ethers, such as, for example, diethyl ether, dioxane or tetrahydrofuran, or chlorohydrocarbons, such as methylene chloride, chloroform or carbon tetrachloride, or amides, such as dimethylformamide or hexamethylphosphoric acid triamide, or acetonitrile or acetone. It is also possible to use mixtures of the solvents mentioned.

Suitable amines are tertiary amines, such as, for example, triethylamine, ethyl-diisopropylamine or tributylamine, but also sterically hindered secondary amines, such as, for example, diisopropylamine. Mixtures of the amines mentioned can also be used.

The reactions can be carried out at temperatures between −80° C. and room temperature. The activation is advantageously carried out with methanesulphonyl chloride in dimethylformamide at −40° C. to −60° C. in the course of 0.2 to 24 hours, preferably 0.5 to 5 hours.

The solvents mentioned in the preparation of the compounds of the formula (IX) or water can be used to dissolve the β-lactam compounds of the formula (XII) for the coupling with the compounds of formula (IXa) or (IXb) to obtain the compounds of formula (X), and the amines mentioned there can be used as the base.

Activation of the carboxylic acids of the general formula (VI) by conversion into an activated ester with, for example, dicyclohexylcarbodiimide, if appropriate in the presence of N-hydroxysuccinimide or 1-hydroxybenzotriazole, is also particularly advantageous.

Suitable solvents here are all the solvents which are also suitable for the preparation of anhydrides of the general formula (IXa,b) and have already been mentioned there.

The reactions can be carried out at temperatures between −30° C. and +100° C. Activation is advantageously carried out with 1-hydroxybenzotriazole and dicyclohexylcarbodiimide in dimethylformamide at room temperature for 2 to 6 hours, and the dicyclohexylurea which has precipitated out is then filtered off with suction and reacted with the β-lactam compounds of the formula (XII) in the form of a solution of their amine salt in the course of 2 to 24 hours. The solvents mentioned for the preparation of the compounds of the formula (IX) can be used to dissolve the β-lactam compounds of the formula (XII), and the amines mentioned there can be used as the base.

The carboxylic acids of the general formula (VI) used as starting substances are known or can be prepared by known methods [DE-OS (German Published Specification) 3,508,258].

The β-lactam compounds of the general formula (VII) and (XII) used as starting substances are known or can be prepared by known methods [U.S. Pat. No. 4,639,448 and DE-OS (German Published Specification) 3,402,642].

The amino-β-lactams of the general formula (VII) used as starting substances are known or can be prepared by known methods [DE-OS (German Published Specification) 3,402,642; U.S. Pat. No. 4,639,448].

The compounds of the general formula I have a broad antibacterial spectrum against Gram-positive and Gram-negative germs and anaerobic bacteria, coupled with a low toxicity. These properties enable them to be used as chemotherapeutic active compounds in human and veterinary medicine.

The compounds according to the invention are active against a very broad spectrum of microorganisms. Gram-negative and Gram-positive bacteria and bacteria-like microorganisms and the diseases caused by these pathogens can be prevented, alleviated and/or cured with the aid of these compounds.

The compounds according to the invention are particularly active against bacteria and bacteria-like microorganisms. They are therefore particularly suitable in human and veterinary medicine for the prophylaxis and chemotherapy of local and systemic infections caused by these pathogens.

For example, local and/or systemic diseases which are caused by the following pathogens or by mixtures of the following pathogens can be treated and/or prevented: Gram-positive cocci, for example Staphylococci (*Staph. aureus* and *Staph. epidermidis*) and Streptococci (*Strept. agalactiae, Strept. faecalis, Strept. pneumoniae* and *Strept. pyogenes*); Gram-negative cocci (*Neisseria gonorrhoeae*) and Gram-negative rod-shaped bacillae, such as Enterobacteriaceae, for example *Escherichia coli Haemophilus influenzae,* Citrobacter (*Citrob. freundii, Citrob. divernis*), Salmonella and Shigella; and furthermore Klebsiella (*Klebs. pneumoniae* and *Klebs. oxytoca*), Enterobacter (*Ent. aerogenes* and *Ent. agglomerans*), Hafnia, Serratia (*Serr. marcescens*), Proteus (*Pr. mirabilis, Pr. rettgeri* and *Pr. vulgaris*), Providencia, Yersinia and the genus Acinetobacter. The antibacterial spectrum moreover includes the genus Pseudomonas (Ps. aeruginosa and Ps. maltophilia) and strictly anaerobic bacteria, such as, for example, Bacteroides fragilis, representatives of the genus Peptococcus, Peptostreptococcus and the genus Clostridium; and furthermore Mycoplasma (*M. pneumoniae, M. hominis* and *M. urealyticum*) and mycobacteria, for example Mycobacterium tuberculosis. The substances according to the invention have an action in particular against Staphylococci, Streptococci, Enterococci and Haemophilus influenzae. On parenteral or, in particular, oral administration, the new compounds have a very good action against microorganisms such as Staphylococci, Streptococci, Enterobacteriaceae, *Escherichia coli,* Klebsiella, Salmonella, Shigella and Proteus.

The above list of pathogens is given merely by way of example and is in no way to be interpreted as limiting. Examples which may be mentioned of diseases which can be caused by the pathogens or mixed infections mentioned and can be prevented, alleviated or cured by the compounds according to the invention are: infection diseases in humans, such as, for example, otitis, pharyngitis, pneumonia, peritonitis, pyelonephritis, cystitis, endocarditis, systemic infections, bronchitis (acute and chronic), septic infections, diseases of the upper respiratory tract, diffuse panbronchiolitis, pulmonary. emphysema, dysentery, enteritis, liver abscesses, urethritis, prostatitis, epididymitis, gastrointestinal infections, bone and joint infections, cystic fibrosis, skin infections, postoperative wound infections, abscesses, phlegmons, wound infections, infected burns, burn wounds, infections iq the oral region, infections following dental operations, osteomyelitis, septic arthritis, cholecystitis, peritonitis with appendicitis, cholangitis, intraabdominal abscesses, pancreatitis, sinusitis, mastoiditis, mastitis, tonsillitis, typhus, meningitis and infections of the nervous system, salpingitis, endometritis, genital infections, pelveoperitonitis and eye infections.

As well as in humans, bacterial infections can also be treated in other species. Examples which may be mentioned are: pigs: coli-diarrhoea, enterotoxaemia, sepsis, dysentery, salmonellosis, metritis-mastitisagalactiae syndrome and mastitis; ruminants (cattle, sheep, goats): diarrhoea, sepsis, bronchopneumonia, salmonellosis, pasteurellosis, mycoplasmosis and genital infections; horses: bronchopneumonia, joint ill, puerperal and post-puerperal infections and salmonellosis; dogs and cats: bronchopneumonia, diarrhoea, dermatitis, otitis, urinary tract infections and prostatitis; poultry (chickens, turkeys, quails, pigeons, ornamental birds and others): mycoplasmosis, *E. coli* infections, chronic respiratory tract infections, slamonellosis, pasteurellosis and psittacosis.

Bacterial diseases in the breeding and rearing of stock and ornamental fish can also be treated, the antibacterial spectrum being ex tended beyond the above-mentioned pathogens to further pathogens, such as, for example, Pasteurella, Brucella, Campylabacter, Listeria, Erysipelothrix, Corynebacteria, Borellia, Treponema, Nocardia, Rickettsia and Yersinia.

The minimum inhibitory concentrations (MIC values, μg/ml) for Example 6 in comparison with Cefaclor [M. Gorman et al., Cefaclor, Chronicles of Drug Discovery, Volume 2, 49, J. Wiley & Sons (1983)] are given in the following tables. The MIC values are determined by the agar dilution test with the aid of a multipoint inoculator, the reading being taken after incubation at 37° C. for 18 to 24 hours. Isosensitest agar is used as the growth medium.

|  | Example 6 | Cefaclor |
|---|---|---|
| *Haemophilus influenzae* No. | | |
| 1 | 1 | 4 |
| 2 | 0.5 | 2 |

|  | Example 6 | Cefaclor |
|---|---|---|
| 4 | 1 | 8 |
| 5 | 0.5 | 4 |
| 6 | 0.5 | 4 |
| 7 | 0.5 | 2 |
| 8 | 0.5 | 1 |
| 9 | 0.5 | 1 |
| 10 | 0.5 | 2 |
| ICB-No. | | |
| *Staph. aureus* | | |
| 25 412 | 32 | 256 |
| 25 413 | 0.5 | 4 |
| 25 414 | 0.5 | 32 |
| 25 417 | ≦0.5 | 4 |
| 25 418 | ≦0.5 | 4 |
| 25 473 | ≦0.5 | 4 |
| 25 559 | ≦0.5 | 8 |
| 25 560 | ≦0.5 | 8 |
| 25 565 | ≦0.5 | 4 |
| 25 568 | ≦0.5 | 4 |
| 25 569 | ≦0.5 | 4 |
| 25 470 | 0.5 | 8 |
| 25 508 | 1 | 8 |
| 25 527 | 2 | 64 |
| 25 397 | ≦0.5 | 8 |
| 25 523 | ≦0.5 | 8 |
| 25 524 | ≦0.5 | 16 |
| 25 525 | ≦0.5 | 4 |
| 25 583 | 4 | 16 |
| ICB-No. | | |
| *Strep. faecalis* | | |
| 27 261 | 8 | >256 |
| 27 249 | 16 | >256 |
| 27 250 | 16 | >256 |
| 27 251 | 32 | >256 |
| 27 252 | 16 | >256 |
| 27 253 | 16 | >256 |
| 27 254 | 16 | >256 |
| 27 255 | 16 | >256 |
| 27 256 | 4 | >256 |
| 27 257 | 4 | >256 |
| ICB-No. | | |
| *Klebs. pneumoniae* | | |
| 6310 | ≦0.5 | 1 |
| 6318 | 4 | 2 |
| 6360 | 64 | 8 |
| 6362 | ≦0.5 | 1 |
| 6379 | ≦0.5 | 1 |
| 6380 | ≦0.5 | 1 |
| ICB-No. | | |
| *E. coli* | | |
| 4895 | 2 | 1 |
| 4322 | 2 | 1 |
| 4800 | 2 | 1 |
| 4815 | 0.5 | 2 |
| Anaerobic bacterie germs | | |
| 1 *Bacteroides fragilis* | 1 | 256 |
| 4 *Bacteroides fragilis* | 0.5 | 128 |
| 6 *Bacteroides fragilis* | 0.5 | 128 |
| 10 *Bacteroides fragilis* | 0.5 | 128 |
| 13 *Bacteroides thetaiotaomicron* | 4 | >256 |
| 15 *Bacteroides distasonis* | ≦0.5 | 2 |
| 16 *Bacteroides ovatus* | 8 | >256 |
| 17 *Clostridium perfringens* | ≦0.5 | 2 |
| 18 *Bacteroides vulgatus* | ≦0.5 | 4 |
| 19 *Clostridium perfringens* | ≦0.5 | ≦0,5 |

The present invention includes pharmaceutical formulations which, in addition to non-toxic, inert pharmaceutically suitable excipients, contain one or more compounds according to the invention or consist of one or more active compounds according to the invention, and relates to processes for the preparation of these formulations.

The present invention also includes pharmaceutical formulations in dosage units. This means that the formulation is in the form of individual parts, for example tablets, dragees, capsules, pills, suppositories and ampoules, the active compound content of which corresponds to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, one half, one third or one quarter of a daily dose.

By non-toxic/inert pharmaceutically suitable excipients there are to be understood solid, semi-solid or liquid diluents, fillers and formulation auxiliaries of all kinds.

Tablets, dragees, capsules, pills, granules, suppositories, solutions, suspensions and emulsions, pastes, ointments, gels, creams, lotions, dusting powders and sprays may be mentioned as preferred pharmaceutical formulations.

Tablets, dragees, capsules, pills and granules can contain the active compound or compounds, in addition to the customary excipients, such as (a) fillers and extenders, for example starches, lactose, sucrose, glucose, mannitol and silicic acid, (b) binders, for example carboxymethylcellulose, alginates, gelatine or polyvinylpyrrolidone, (c) humectants, for example glycerol (d) disintegrating agents, for example agar-agar, calcium carbonate and sodium carbonate, (e) solution retarders, for example paraffin and (f) absorption accelerators, for example quaternary ammonium compounds, (g) wetting agents, for example cetyl alcohol and glycerol monostearate, (h) adsorbents, for example kaolin and bentonite and (i) lubricants, for example talc, calcium stearate and magnesium stearate and solid polyethylene glycols, or mixtures of the substances mentioned under (a) to (i).

The tablets, dragees, capsules, pills and granules can be provided with the customary coatings and shells, optionally containing opacifying agents, and can also be of such composition that they release the active compound or compounds only or preferentially in a certain part of the intestinal tract, if appropriate in a delayed manner, examples of embedding compositions which can be used being polymeric substances and waxes.

The active compound or compounds can also be in microencapsulated form, if appropriate with one or more of the abovementioned excipients.

Suppositories can contain, in addition to the active compound or compounds, the customary water-soluble or water-insoluble excipients, for example polyethylene glycols, fats, for example cocoa fat, and higher esters (for example $C_{14}$-alcohol with $C_{16}$-fatty acid), or mixtures of these substances.

Ointments, pastes, creams and gels can contain, in addition to the active compound or compounds, the customary excipients, for example animal and vegetable fats, waxes, paraffins, starch, tragacanth, cellulose derivatives, polyethylene glycols, silicones, bentonites, silicic acid, talc and zinc oxide, or mixtures of these substances.

Dusting powders and sprays can contain, in addition to the active compound or compounds, the customary excipients, for example lactose, talc, silicic acid, aluminum hydroxide, calcium silicate and polyamide powder, or mixtures of these substances. Sprays can additionally contain the customary propellants, for example chlorofluorohydrocarbons.

Solutions and emulsions can contain, in addition to the active compound or compounds, the customary excipients, such as solvents, solubilizing agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, in particular cottonseed oil, groundnut oil, corn germ oil, olive oil, castor oil and sesame oil, glycerol, glycerolformal, tetrahydrofurfuryl alcohol, polyethylene glycols and fatty acid esters of sorbitan, or mixtures of these substances.

For parenteral administration, the solutions and emulsions can also be in a sterile form which is isotonic with blood.

Suspensions can contain, in addition to the active compound or compounds, the customary excipients, such as liquid diluents, for example water, ethyl alcohol or propylene glycol, suspending agents, for example ethoxylated isostearyl alcohols, polyoxyethylene sorbitol and sorbitan esters, microcrystalline cellulose, aluminum metahydroxide, bentonite, agar-agar and tragacanth, or mixtures of these substances.

The formulation forms mentioned can also contain colouring agents, preservatives and additives which improve the smell and taste, for example peppermint oil and eucalyptus oil, and sweeteners, for example saccharin.

The therapeutically active compounds should preferably be present in the abovementioned pharmaceutical formulations in a concentration of about 0.1 to 99.5, preferably about 0.5 to 95% by weight of the total mixture.

The abovementioned pharmaceutical formulations can also contain other pharmaceutically active compounds in addition to the compounds according to the invention.

The abovementioned pharmaceutical formulations are prepared in the customary manner by known methods, for example by mixing the active compound or compounds with the excipient or excipients.

The formulations mentioned can be used on humans and animals either orally, rectally, parenterally (intravenously, intramuscularly or subcutaneously), intracisternally, intravaginally, intraperitoneally or locally (dusting powders, ointments, drops) and for the therapy of infections in hollow spaces and body cavities. Suitable formulations are injection solutions, solutions and suspensions for oral therapy, gels, infusion formulations, emulsions, ointments or drops. Ophthalmological and dermatological formulations, silver salts and other salts, eardrops, eye ointments, dusting powders or solutions can be used for local therapy. In the case of animals, intake can also be via the feed or drinking water, in suitable formulations.

Gels, powders, dusting powders, tablets, sustained release tablets, premixes, concentrates, granules, pellets, boli, capsules, aerosols, sprays and inhalates can furthermore be used on humans and animals. The compounds according to the invention can furthermore be incorporated into other carrier materials, such as, for example, plastics (chains of plastic for local therapy), collagen or bone cement.

In general, it has proved advantageous both in human and in veterinary medicine to administer the active compound or compounds according to the invention in total amounts of about 0.5 to about 500, preferably 5 to 100 mg/kg of body weight every 24 hours, if appropriate in the form of several individual doses, in order to achieve the desired results. An individual dose preferably contains the active compound or compounds according to the invention in amounts of about 1 to about 80, in particular 3 to 30 mg/kg of body weight. However, it may be necessary to deviate from the dosages mentioned, and in particular to do so as a function of the nature and body weight of the subject to be treated, the nature and severity of the disease, the nature of the formulation and of the administration of the medicament and the period or interval within which administration takes place.

Thus, in some cases it may suffice to manage with less than the abovementioned amount of active compound, whilst in other cases the abovementioned amount of active compound must be exceeded. The particular optimum dosage required and mode of administration of the active compounds can easily be specified by any expert on the basis of his expert knowledge.

The new compounds can be administered in the customary concentrations and formulations together with the feed or with feed formulations or with the drinking water. Infection by Gram-negative or Gram-positive bacteria can thereby be prevented, alleviated and/or cured, and a promotion in growth and an improvement in feed conversion can thereby be achieved.

The compounds according to the invention can be combined with other antimicrobial active compounds and lactamase inhibitors, for example with penicillins which are particularly penicillinase-resistant and clavulanic acid, for the purpose of increasing the action spectrum and in order to achieve an increase in action, especially against $\beta$-lactamase-forming bacteria. Such a combination would be, for example, that with oxacillin or dicloxacillin.

The compounds according to the invention can also be combined with aminoglycoside antibiotics, such as, for example, gentamicin, sisomicin, canamicin, amicacin or tobramycin, for the purpose of broadening the action spectrum and achieving an increase in action.

PREPARATION EXAMPLES

Example 1

Benzhydryl 7-amino-3-chloromethyl-3-cephem-4-carboxylate

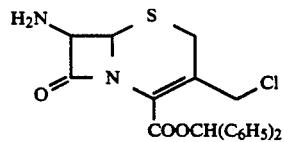

19.64 ml (0.242 mol) of pyridine are added to a suspension of 50 g (0.0972 mol) of benzhydryl 7-phenylacetamido-3-hydroxymethyl-3-cephem-4-carboxylate in 500 ml of methylene chloride at room temperature. After cooling to $-20°$ C., 40.48 g (0.0972 mol) of phosphorus pentachloride are added and the mixture is stirred at $-20°$ C. for 5 minutes. The mixture is warmed to $0°$ C. with an icebath and stirred for 10 minutes, and is then warmed to $15°$ C. with a waterbath and stirred for 1 hour. Thereafter, the mixture is cooled to $-70°$ C. and 720 ml of cold methanol are quickly added The mixture is then stirred at $-70°$ C. for 5 minutes, at $0°$ C. for 10 minutes and at $+15°$ C. for 25 minutes. The solution is subsequently concentrated to a high degree in vacuo and 1,400 ml of saturated sodium bicarbonate solution are added. The solution is extracted three times with methylene chloride and the organic phase is dried with sodium sulphate and concentrated in vacuo. The crude product is chromatographed on 500 g of silica gel 60 (0.04–0.063 mm) with methylene chloride.

Yield: 29.0 g (72% of theory)
$C_{21}H_{19}ClN_2O_3S$ (414.9)

NMR ($CDCl_3$): $\delta$=2.06 (s, 2H); 3.45 (d, 1H); 3.62 (d, 1H); 4.25–4.41 (q, 2H); 4.75 (d, 1H); 4.93 (d, 1H); 6.97 (s, 1H); 7.25–7.46 (m, 10H) ppm.

Example 2

Benzhydryl D-7-[2-(t-butoxycarbonylamino)-2-(2-aminobenzothiazol-6-yl)-glycylamido]-3-chloromethyl-3-cephem-4-carboxylate

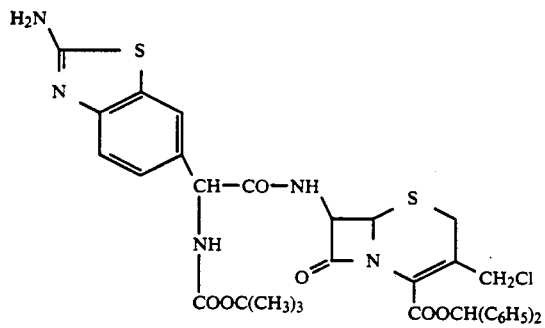

18.07 g (0.0875 mol) of N,N'-dicyclohexylcarbodiimide (DCC), dissolved in 150 ml of tetrahydrofuran, are added to a mixture of 28.3 g (0.0875 mol) of D-α-t-butoxycarbonylamino-α-(2-aminobenzothiazol-6-yl)acetic acid and 24.1 g (0.058 mol) of benzhydryl 7-amino-3-chloromethyl-3-cephem-4-carboxylate (Example 1) in 136 ml of tetrahydrofuran and 77 ml of dimethylformamide at 0° C. and the mixture is then stirred at room temperature for 2 hours and concentrated to dryness. The residue is suspended in 1,200 ml of ethyl acetate, the suspension is stirred for 10 minutes and undissolved constituents are then removed by filtration with suction. After distilling off the ethyl acetate, the residue is chromatographed on silica gel 60 (0.04–0.063 mm) with toluene/ethyl acetate (1:1)

Yield: 17.6 g (42% of theory)
$C_{35}H_{34}ClN_5S_2O_6$ (720.3)

NMR (DMSO): $\delta$=1.37 (s, 9H); 3.46 (d, 1H); 3.64 (d, 1H); 4.32–4.43 (q, 2H); 5.11 (d, 5 Hz, 1H); 5.31 (d, 1H); 5.8–5.86 (q, 1H); 6.98 (s, 1H); 7.15–7.5 (mm, 14H); 7.67 (s, 1H) ppm

Example 3

Benzhydryl D-7-[2-(t-butoxycarbonylamino)-2-(2-aminobenzothiazol-6-yl)glycylamido]-3-iodomethyl-3-cephem-4-carboxylate

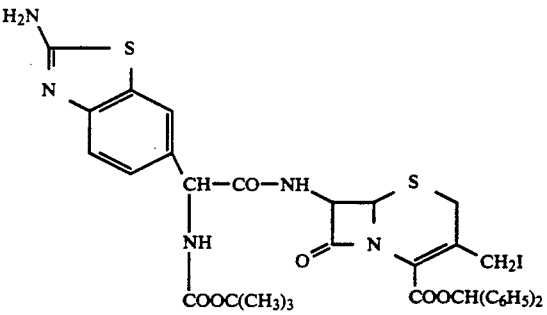

A mixture of 20.3 g (0.0282 mol) of benzhydryl D-7-[2-(t-butoxycarbonylamino)-2-(2-aminobenzothiazol-6-yl)-glycylamido]-3-chloromethyl-3-cephem-4-carboxylate (Example 2) and 12.68 g (0.0846 mol) of sodium iodide in 300 ml of acetone is stirred at room temperature for 2 hours and evaporated to dryness. The residue is taken up in 500 ml of ethyl acetate and the mixtre is washed with aqueous sodium thiosulphate solution, water and sodium chloride solution. After drying over sodium sulphate, the solvent is distilled off and the residue is digested in ether.

Yield 22 g

The compound is used directly in the next stage.

Example 4

Benzhydryl D-7-[2-(t-butoxycarbonylamino)-2-(2-aminobenzothiazol-6-yl)glycylamido]-3-(triphenylphosphonio)methyl-3-cephem-4-carboxylate iodide

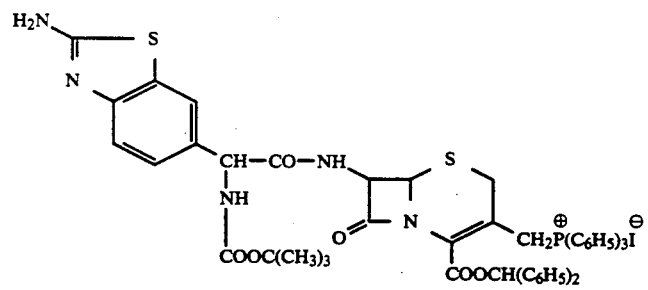

A mixture of 22 g (0.0271 mol) of benzhydryl D-7-2-(t-butoxycarbonylamino)-2-(2-aminobenzothiazol-6-yl)glycylamido]-3-iodomethyl-3-cephem-4-carboxylate (Example 3) and 21.32 g (0.0813 mol) of triphenylphosphine in 500 ml of ethyl acetate is stirred at room temperature for 1 hour. After 30 minutes, the product precipitates out. The mixture is concentrated to about 150 ml under reduced pressure and 500 ml of ether are added to the concentrate. The resulting precipitate is filtered off with suction and rinsed with ether.

Yield: 19.6 g (67% of theory)
$C_{53}H_{49}IN_5O_6PS_2$ (1074.1)

NMR (DMSO): $\delta$=1.35 (S, 9H); 3.3–3.42 (dd, 2H); 4.81–4.93 (t, 2H); 5.2 (d, 1H); 5.33 (d, 1H); 5.72–5.79 (q, 1H); 6.24 (s, 1H); 7.2–7.49 (mm, 15H); 7.6–7.79 (m, 1H) ppm.

Example 5

Benzhydryl D-7-[2-(t-butoxycarbonylamino)-2-(2-aminobenzothiazol-6-yl)glycylamido]-3-[(Z)-1-propen-1-yl]-3-cephem-4-carboxylate

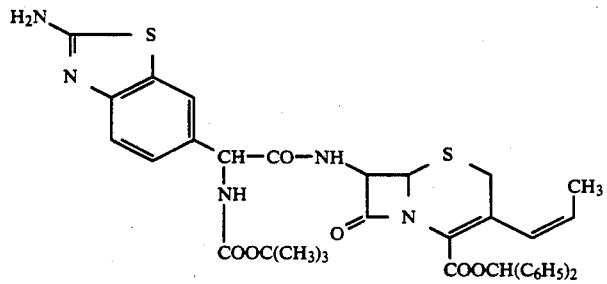

7.04 ml (0.126 mol) of acetaldehyde and 7.6 g (0.007 mol) of benzhydryl D-7-[2-(t-butoxycarbonylamino)-2-(2-aminobenzothiazol-6-yl)glycylamido]-3-(triphenylphosphonio)methyl-3-cephem-4-carboxylate iodide (Example 4) are added to a cold solution of 6.08 g (0.07 mol) of lithium bromide in 50 ml of dimethylformamide and 150 ml of methylene chloride at −5° C. The mixture is stirred at −5° C. for 20 hours and then at room temperature for 5 hours. The solution is concentrated to about 50 ml in vacuo and the concentrate is partitioned in a solvent mixture of 200 ml of ethyl acetate and 200 ml of water. The upper layer is separated off and washed once with aqueous sodium chloride solution. After drying over sodium sulphate and distilling off the solvent, the residue is taken up in toluene and the mixture is introduced onto a column packed with silica gel (0.04–0.063 mm). The column is eluted first with toluene and then with the solvent mixture toluene/ethyl acetate (5:1) and toluene/ethyl acetate (1:1).

Yield: 2.9 g (58% of theory)
$C_{37}H_{37}N_5O_6S_2$ (711.9)
NMR (CDCl$_3$): δ=1.35 (dd, 3H); 1.43 (s, 9H); 3.15 (d, 1H); 3.31 (d, 1H); 4.97 (d, 1H); 5.3 (s, 1H); 5.46–5.55 (m, 1H); 5.71 (broad s, 2H); 5.78–5.85 (q, 1H); 6.03 (d, J=11 Hz, 1H); 6.87 (s, 1H); 7.2–7.4 (mm, 12H); 7.5 (s, 1H) ppm.

Example 6

D-7-[(2-Aminobenzothiazol-6-yl)glycylamido]-3-[(Z)-1-propen-1-yl]-3-cephem-4-carboxylic acid, cis-isomer yl)glycylamido]-3-[(Z)-1-propen-1-yl]-3-cephem-4-carboxylate (Example 5) are dissolved in 20 ml of methylene chloride, 40 ml of trifluoroacetic acid (TFA) are added and the mixture is stirred with a magnetic stirrer at room temperature for 60 minutes. The methylene chloride and trifluoroacetic acid are removed in vacuo, the semi-solid red oil which remains is triturated in ether and the product is filtered off with suction and washed with ether. The pale yellow trifluoroacetate is dried in vacuo and then suspended in 100 ml of water and the insoluble yellow flocks are filtered off with suction over kieselguhr and rinsed with 30 ml of water. The still slightly cloudy solution is filtered again over a membrane filter (Millipore, 0.45 μm). The filtrate is pumped onto an RP 18 column (Hibar 250-25, Merck). The column is eluted first with 200 ml of water (fraction 1), then with 400 ml of 5% strength methanol (fraction 2) and finally with 10% strength methanol, in each case 300 ml fractions being collected (fraction 3 to 12). The fractions are investigated by means of analytical HPLC and fractions 6 to 10, which contain the desired peak, are combined, the methanol is distilled off in vacuo and the residue is lyophilized.

Yield: 400 mg
$C_{19}H_{19}N_5O_4S_2$ (445.5)
NMR (DCOOD): δ=1.67 (dd, 3H); 3.41 (d, 1H); 3.55 (d, 1H); 5.3 (d, 1H); 5.78 (s, 1H); 5.81-5.91 (q and m, 2H); 6.25 (d, J=11.6 Hz, 1H); 7.81–7.9 (q, 2H); 8.18 (s, 1H) ppm.

Analytical HPLC: Hibar 250-4, RP-8, 10 μm, 254 nm
Mobile phase: 1,000 ml of CH$_3$CN-30 ml of acetic acid—870 ml of water
Flow rate: 4 ml/minute, concentration: 1 mg/ml
Retention: 3.22 (content: 97.3%)

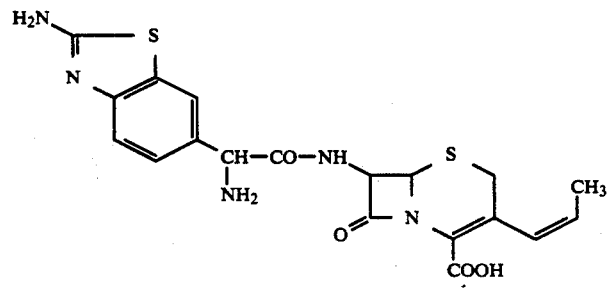

2.9 g (4.1 mmol) of benzhydryl D-7-[2-(t-butoxycarbonylamino)-2-(2-aminobenzothiazol-6-

Example 7

D-7-[(2-Aminobenzothiazol-6-yl)glycylamido]-3-[(E)-1-propen-1-yl]-3-cephem-4-carboxylic acid, trans-isomer

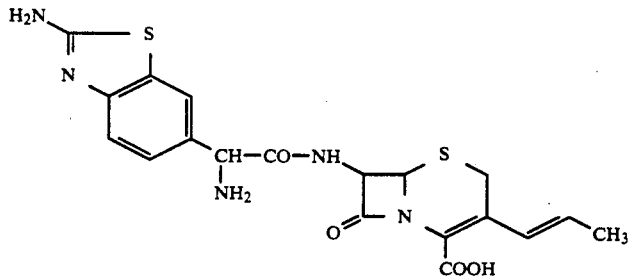

The E-isomer compound is obtained from the preparative high pressure liquid chromatography of D-7-[(2-aminobenzothiazol-6-yl)glycylamido]-3-[(Z)-1-propen-1-yl]-3-cephem-4-carboxylic acid (cis-isomer; Example 6) by further elution with 30% strength methanol.

Yield: 137 mg
$C_{19}H_{19}N_5O_4S_2$ (445.5)
NMR (DCOOD): $\delta$=1.9 (d, 3H); 3.61 (s, 2H); 5.25 (d, 1H); 5.72 (s, 1H); 5.87 (d, 1H); 6.23–6.46 (m, 1H); 7.04 (d, J=15.8 Hz, 1H); 7.8–7.88 (q, 2H); 8.18 (s, 1H) ppm.

Analytical HPLC: Hibar 250-4, RP-8 10 µm, 254 nm
Mobile phase: 100 ml of CH$_3$CN-30 ml of acetic acid—870 ml of water
Flow rate: 4 ml/minute, concentration: 1 mg/ml
Retention: 5.20 (content: 67.2%)

Example 8

Benzhydryl 7phenylacetamido-3-(triphenylphosphonio)methyl-3-cephem-4-carboxylate iodide

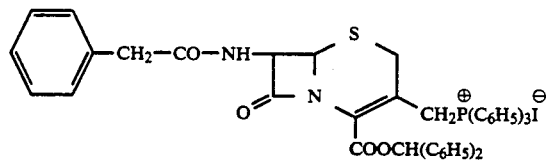

32.5 g (0.0609 mol) of benzhydryl 7-phenylacetamido-3-chloromethyl-3-cephem-4-carboxylate are dissolved in 330 ml of acetone, and 10.1 g (0.0674 mol) of NaI and 17.6 g (0.0671 mol) of triphenylphosphine are added in succession, with stirring. After the mixture has been stirred at room temperature for 1.5 hours, the insoluble material is removed by filtration with suction and the clear mother liquor is stirred into 1,000 ml of ether. The white flocculent material which precipitates out is filtered off with suction, washed with 300 ml of ether and dried in vacuo.

Yield: 51 g (94% of theory)
$C_{47}H_{40}IN_2O_4PS$ (886.8)
NMR (DMSO): $\delta$=3.51–3.61 (q, 4H); 4.93–5.05 (t, 1H); 5.22–5.33 (d and t, 2H); 5.7–5.76 (q, 1H); 6.26 (s, 1H); 7.21–7.46 (mm, 15H); 7.68–7.79 (m, 15H); 9.14 (d, 1H) ppm.

Example 9

I. Benzhydryl 7-phenylacetamido-3-[(Z)-propen-1-yl]-3-cephem-4-carboxylate

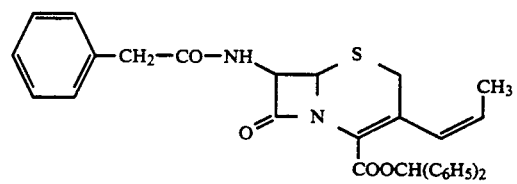

15.9 g (17.9 mmol) of benzhydryl 7-phenylacetamido-3-(triphenylphosphonio)methyl-3-cephem-4-carboxylate iodide (Example 8) are taken in 100 ml of methylene chloride and 12.8 ml (229.6 mmol) of acetaldehyde in a 250 ml three-necked flask. The mixture is cooled to 0° C. and 100 ml of water are added. 16.3 ml of 1N NaOH are then added dropwise in the course of 4 hours, while keeping the pH constant at 8.6. The reaction solution is diluted with methylene chloride and the organic phase is separated off, washed once with water and then dried over sodium sulphate. After the drying agent has been removed, a further 13 ml (233 mmol) of acetaldehyde are added to the methylene chloride solution and the mixture is stirred overnight. The reaction solution is then concentrated to dryness, the residue is dissolved again in a little methylene chloride and the solution is introduced onto a column filled with 500 ml of silica gel (0.04–0.063 mm). 400 ml fractions are collected and all the fractions are investigated for the cis-isomer compound by means of analytical HPLC.

Analytical HPLC: Hibar 250-4, Lichrosorb Si 60, 5 µm, 254 nm
Mobile phase: 100 ml of methylene chloride—3 ml of methanol
Flow rate: 2 ml/minute, concentration: 1 mg/ml
Retention: 5.80 (content 73.1%)
Yield: 4.75 g (51% of theory)
$C_{31}H_{28}N_2O_4S$ (524.6)
NMR (CDCl$_3$): $\delta$=1.4 (dd, 3H); 3.22 (d, 1H); 3.41 (d, 1H); 3.65 (q, 2H); 5.0 (d, 1H); 5.48–5.6 (m, 1H); 6.07 (d, 1H); 6.92 (s, 1H); 7.21–7.4 (m, 15H) ppm.

II. Benzhydryl 7-phenylacetamido-3-[(Z)-propen-1-yl]-3-cephem-4-carboxylate (different process)

177.2 g (0.2 mol) of benzhydryl 7-phenylacetamino-3-(triphenylphosphonio)methyl-3-cephem-4-carboxylate iodide are dissolved almost completely in 800 ml of CH$_2$Cl$_2$ and 80 ml of CH$_3$OH, the solution is cooled to +5° C. and 167.8 ml (3.0 mol) of acetaldehyde are added; during this operation, the temperature should not rise above 20° C.

26.4 g (0.25 mol) of sodium carbonate, dissolved in 200 ml of water, are then slowly added at 14° C. in the course of 15 minutes. The icebath is subsequently removed and the solution is stirred at room temperature for 2½ hours.

The course of the reaction is checked by thin layer chromatography in acetonitrile: water=9:1 and toluene: ethyl acetate=8:2. When the Wittig reaction has ended, the organic phase is separated off and the aqueous phase is washed again with $CH_2Cl_2$. The combined $CH_2Cl_2$ phases are filtered over 150 g of silica gel (Merck, 0.04–0.063 mm) and the residue is rinsed with $CH_2Cl_2$ (about 1,000 ml) until the filtrate is colorless.

The $CH_2Cl_2$ filtrate is dried over $Na_2SO_4$ and then concentrated to an oily residue and the residue is stirred with 800 ml of ethanol. The ethanolic solution is stirred on a rotary evaporator for 15 minutes, the product gradually crystallizing out. Removal of ethanol by distillation is continued and the crystal sludge formed is stirred with about 90 ml of ether/100 ml of n-pentane, filtered off with suction and rinsed with 60 ml of n-pentane. The product is dried over $P_4O_{10}$ in vacuo overnight.

Yield: 41.2 g (39.2% of theory), analytical HPLC: Hibar 250-4; Lichrosorb Si 60, 5 μm, 254 nm.

Mobile phase: 850 ml of toluene—150 ml of ethyl acetate

Flow rate: 2 ml min$^{-1}$

Retention: 4.73 (80.2%; Z-isomer), 4.00 (17.4%; E-isomer).

Example 10

I. Benzhydryl 7-amino-3-[(Z)-1-propen-1-yl]-3-cephem-4-carboxylate

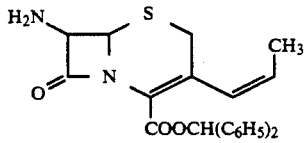

6.4 (12.2 mmol) of benzhydryl 7-phenylacetamido-3-[(Z)-propen-1-yl]-3-cephem-4-carboxylate (Example 9) are dissolved in 64 ml of methylene chloride, the solution is cooled to −40° C. with a dry ice bath and 2.47 ml (30.5 mmol) of pyridine and 2.54 g (12.2 mmol) of phosphorus pentachloride are added in succession. After 5 minutes, the mixture is allowed to warm to −20° C., after which the temperature should rise to −10° C. in the course of 20 minutes and then rise to +10° C. The solution is now stirred at +10° C. to +15° C. for 1 hour. The mixture is subsequently cooled to −40° C., 100 ml of methanol (−30° C.) are added and the mixture is stirred at +10° C. for a further 30 minutes. The reaction solution is concentrated gently, the oil obtained is dissolved in 600 ml of methylene chloride, the solution is stirred into 800 ml of sodium bicarbonate solution and the mixture is stirred for 10 minutes. The methylene chloride phase is separated off, washed once with water and dried over sodium sulphate. The methylene chloride filtrate is chromatographed on 400 ml of silica gel (0.04–0.063 mm), elution being carried out first with methylene chloride and then with methylene chloride with the addition of methanol (gradient up to 10%). The eluate is investigated by means of analytical HPLC and TLC (thin layer chromatography) (methylene chloride/methanol=100:1).

Yield: 4.2 g $C_{23}H_{22}N_2O_3S$ (406.5)

NMR (CDCl$_3$): δ=1.4 (dd, J=2 Hz and 7 Hz, 3H); 3.3 (d, J=17 Hz, 1H); 3.48 (d, J=17 Hz, 1H); 4.75 (d, J=4.5 Hz, 1H); 4.98 (d, J=4.5 Hz, 1H); 5.45-5.55 (d and q, J=10 Hz and 7 Hz, 1H); 6.07 (d, J=11 Hz, 1H); 6.96 (s, 1H); 7.23-7.42 (m, 10H); 8.6 (d, 2H) ppm.

Analytical HPLC: Hibar 250-4, Merck, Lichrosorb Si 60, 5 μm, 254 nm

Mobile phase: 1,000 ml of methylene chloride-5 ml of methanol

Flow rate: 2 ml/min, concentration 1 mg/m

Retention: 12.75 (content: 70.4%)

II. Benzhydryl 7-amino-3-[(Z)-1-propen-1-yl]-3-cephem-b 4-carboxylate hydrochloride (different process)

187.05 g (0.8976 mol; 1.57 equivalents) of phosphorus pentachloride are taken in 3,300 ml of $CH_2Cl_2$ in a 4 l three-necked flask at room temperature and 66.42 ml (0.821 mol; 1.44 equivalents) of pyridine, dissolved in 330 ml of $CH_2Cl_2$, are added dropwise in the course of 5-10 minutes, whereupon the temperature rises to 24°-27° C. and a clear colorless solution is formed. The solution is cooled to −2° C. and 300 g (0.572 mol) of benzhydryl 7-phehylacetamido-3-[(Z)-propen-1-yl]-3-cephem-4-carboxylate are added, during which the temperature should not rise above +2° C. Thereafter, the cooling bath is removed and the mixture is stirred for 40 minutes, during which the temperature of the reaction solution rises to 10°-12° C. (imino chloride solution).

255 ml (2.843 mol; 4.99 equivalents) of 1,3-butanediol, dissolved in 1,650 ml of $CH_2Cl_2$, are cooled to −20° C. to −25° C. (acetone/dry ice) in a 6l three-necked flask and the imino chloride solution is introduced into this solution by means of a vacuum in the course of 5-10 minutes. The temperature should not thereby rise above −20° C. The low temperature bath is then removed and the reaction solution is stirred for 2 hours, during which the temperature rises to 10° C.

The reaction solution is now washed with 1,200 ml of ice-water and with 1,200 ml of 2N HCl and 1,200 ml of saturated sodium chloride solution. The $CH_2Cl_2$ phase is dried briefly over $Na_2SO_4$, the drying agent is separated off and the filtrate is concentrated to dryness. The crystalline material which has precipitated out is stirred with 1,200 ml to 2,000 ml of ethyl acetate and then filtered off with suction and rinsed with ether. The product is dried overnight under a high vacuum:

Yield: 173.9 g (68.7% of theory)

$C_{23}H_{23}ClN_2O_3S$ (442.96)

NMR (DMSO): δ=1.48 (dd,3H); 3.56 (d,1H); 3.79 (d,1H); 5.2 (d,1H); 5.31 (d,1H); 5.56-5.72 (m,1H); 6.21 (weak d, 1H); 6.28 (weak d,1H); 6.91 (s,1H); 7.25-7.47 (m,10H) ppm.

As well as the Z-isomer, the product contains some E-isomer (Z/E=91:9).

Example 11

Benzhydryl
D-7-[2-(t-butoxycarbonylamino)-2-(2-aminobenzothiazol-6-yl)glycylamido]-3-[(Z)-1-propen-1-yl]-3-cephem-4-carboxylate

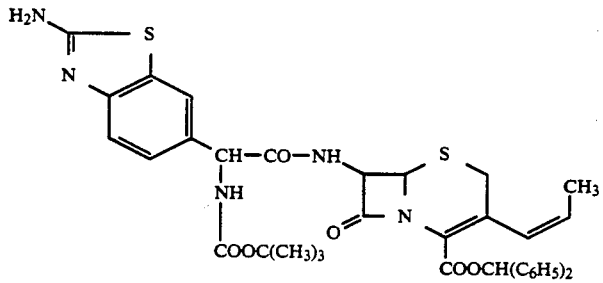

3.4 g (10.5 mmol) of D-α-t-butoxycarbonylamino-α-(2-aminobenzothiazol-6-yl)acetic acid and 4.0 g (7 mmol) of benzhydryl 7-amino-3-[(Z)-1-propen-1-yl]-3-cephem-4-carboxylate (Example 10) are dissolved in 100 ml of tetrahydrofuran. 2.2 g (10.5 mmol) of DCC are added to the clear yellow solution and the mixture is then stirred at room temperature for 2 hours. After stirring for two . hours, the mixture is concentrated to dryness, the residue is suspended in 150 ml of ethyl acetate, the suspension is stirred with a magnetic stirrer for 10 minutes and the insoluble constituents are removed by filtration with suction. The ethyl acetate filtrate is concentrated to dryness, the residue is dissolved in 50 ml of methylene chloride and the solution is chromatographed on 200 ml of silica gel (0.04–0.063 mm). Elution is carried out with methylene chloride and methylene chloride/methanol mixtures in the following sequence:

1. Methylene chloride (fraction 1 to 6): 200 mg, discarded
2. Methylene chloride—2% methanol (fraction 7, 8): 200 mg, discarded
3. Methylene chloride—3% to 4% methanol (fraction 9, 10)
4. Methylene chloride—4% to 5% methanol (fraction 11 to 13)
   Yield of fraction 9 to 13:3.1 g
5. Methylene chloride—5% to 10% methanol (fraction 14,15): 1.9 g
6. Methylene chloride—methanol (1:1, fraction 16): 0.7 g, discarded According to investigation by analytical HPLC, fractions 9 to 13 contain the desired compound.
Yield: 3.1 g (44% of theory)
$C_{37}H_{37}N_5O_6S_2$ (711.9)
NMR (CDCl$_3$): = 1.35 (dd, 3H); 1.43 (s, 9H); 3.15 (d, 1H); 3.31 (d, 1H); 4.97 (d, 1H); 5.3 (s, 1H); 5.46–5.55 (m, 1H); 5.71 (broad s, 2H); 5.7–5.85 (q, 1H); 6.03 (broad d, J=11 Hz, 1H); 6.87 (s, 1H); 7.2–7.4 (mm, 12H); 7.5 (s, 1H) ppm.

Example 12

D-7-[(2-Aminobenzothiazol-6-yl)glycylamido]-3-[(Z)-1-propen-1-yl]-3-cephem-4-carboxylic acid trifluoroacetate

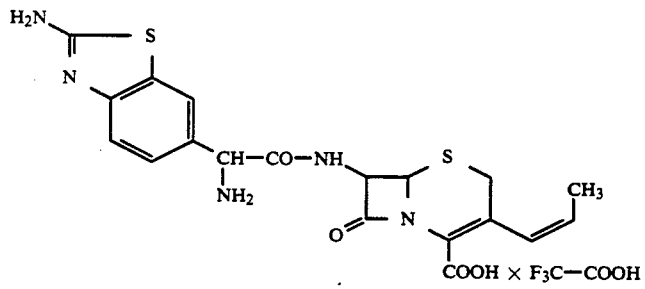

3.1 g (4.35 mmol) of diphenylmethyl D-7-[2-(t-butoxycarbonylamino)-2-(2-aminobenzothiazol-6-yl)glycylamido]-3-[(Z)-1-propen-1-yl]-3-cephem-4-carboxylate (Example 11) are dissolved in 20 ml of methylene chloride, 50 ml of trifluoroacetic acid and 5 ml of anisole are added and the mixture is stirred at room temperature for 60 minutes. The mixture is concentrated in vacuo, 200 ml of ether are added to the concentrate and the solid which has precipitated out is filtered off and rinsed with 100 ml of ether. The pale yellow trifluoroacetate is dried in vacuo.

Yield: 2.7 g
$C_{21}H_{21}F_3N_5O_6S_2$ (560.6)
Analytical HPLC: Hibar 250-4, Merck RP-8, 10 μm, 254 nm
Mobile phase: 250 ml of $CH_3CN$—75 ml of glacial acetic acid—2,175 ml of water
Flow rate: 4 ml/min, concentration: 1 mg/ml
Retention 3.33 (content: 76.4%)

Example 13

D-7-[(2-Aminobenzothiazol-6-yl)glycylamido]-3-[(Z)-1-propen-1-yl]-3-cephem-4-carboxylic acid

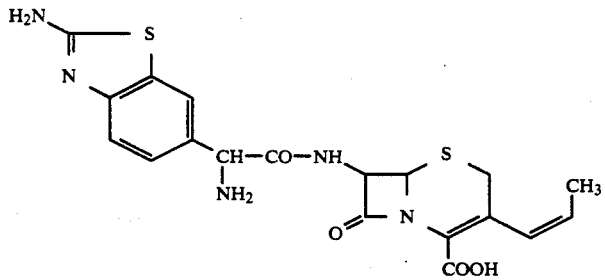

2.6 g (4.64 mmol) of D-7-[(2-aminobenzothiazol-6-yl)glycylamido]-3-[(Z)-1-propen-1-yl]-3-cephem-4-carboxylic acid trifluoroacetate (Example 12) are suspended in 100 ml of water and the small yellow insoluble particles are removed over kieselguhr and rinsed with 30 ml of water. The still slightly cloudy solution is filtered over a membrane filter (Millipore, 0.45 μm) and the 3-propenylcephalosporin is isolated from the filtrate by means of preparative HPLC analogously to Example 6.

Yield: 500 mg
$C_{19}H_{19}N_5O_4S_2$ (445.5)

NMR (DCOOD): δ=1.67 (dd, 3H); 3.41 (d, 1H); 3.55 (d, 1H); 5.3 (d, 1H); 5.78 (s, 1H); 5.81–5.91 (q and m, 2H); 6.25 (broad d, J=11.6 Hz, 1H); 7.81–7.9 (q, 2H); 8.18 (s, 1H) ppm.

Example 14

Sodium salt of D-α-[(1-methyl-2-methoxycarbonyl-vinyl)amino]-(2-aminobenzothiazol-6-yl)acetic acid

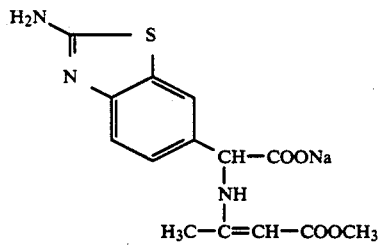

100 g [corresponding to 97.2 g (0.435 mol)] of D-2-aminobenzothiazol-6-yl)glycine (content=97.2%, enantiomeric excess=89.7%) are introduced into methanolic sodium hydroxide solution prepared from 18.6 g (0.465 mol, that is to say 7% excess) of NaOH and 1,000 ml of methanol. While boiling under reflux and stirring, a clear solution forms, and to this is added 64 ml (0.59 mol, about 40% excess) of methyl acetoacetate, dissolved in 100 ml of methanol, in the course of 40 minutes (pH when the dropwise addition has ended=10.3; sample/water=1:1). The solution is then heated under reflux for 1 hour and stirring is subsequently continued without heating for several hours. The material which has crystallized out is filtered off with suction and washed with toluene (two portions of 200 ml). The residue on the filter is heated to the boiling point in 1,000 ml of toluene for 30–40 minutes, 300 ml of toluene are then distilled off and the mixture is washed by dropwise addition of fresh toluene and is dried in a fresh air cabinet at 70° C. overnight.

Yield: 81.9 g (52.1% of theory)
$C_{14}H_{14}N_3O_4SNa.H_2O$ (361.4)

Calculated: C 46.53, H 4.46, N 11.62, S 8.87, Na 6.36.
Found: C 46.2, H 4.4, N 11.9, S 8.4, Na 5.6, Br 0.1 Cl 0.5.

NHR (DMSO): δ=1.63 (s, 3H); 3.49 (s, 3H); 4.25 (s, 1H); 4.7 (d, J=7.5 Hz, 1H); 7.12 (dd, 1H); 7.21 (d, 1H); 7.34 (s, 2H); 7.48 (s, 1H); 9.55 (d, 1H) ppm.

ee=100%

Example 15

7-Amino-3-[(Z)-1-propen-1-yl]-3-cephem-4-carboxylic acid (7-APCA)

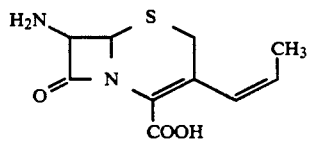

54.5 g (0.123 mol of benzhydryl 7-amino-3-[(Z)-1-propen-1-yl]-3-cephem-4-carboxylate (Example 10) are added to a stirred solution of 500 ml of trifluoroacetic acid (TFA) and 31 ml of anisole, which is cooled to 0° C. The mixture is stirred at room temperature for 1 hour and is then concentrated in vacuo at 30° C. and the oily residue is stirred with 600 ml of ether for 1 hour. The precipitate is filtered off with suction and washed with 300 to 400 ml of ether and the residue on the filter is dried in vacuo for 3 hours. The trifluoroacetate is suspended in 300 ml of water, the suspension is cooled to +5° C. and the pH is brought to 0.2–0.4 with 12N HCl. The resulting clear solution is cooled to +5° C. and stirred with 4 g of active charcoal for 10 minutes. The active charcoal is filtered off with suction over kieselguhr and rinsed with about 50 ml of 0.1N HCl. The filtrate is brought to pH 2.1 at +5° C. with 20% strength NaOH and the product which has precipitated out is left to stand in a refrigerator for 1 hour in order to bring the crystallization to completion. The crystal sludge is filtered off with suction, washed with 100 ml of water and 300 ml of acetone and dried in vacuo.

Yield: 16.4 g (55.4% of theory)
$C_{10}H_{12}N_2O_3S$ (240.3)

NMR (DCOOD): δ=1.8 (dd, 3H); 3.61 (d, 1H); 3.77 (d, 1H); 5.39 (d, 1H); 5.52 (d, 1H); 5.91–6.06 (q, 1H); 6.5 (d, 1H) ppm.

Analytical HPLC: Hibar 250-4, Merck RP-8, 10 μm, 254 nm

Mobile phase: 100 ml of $CH_3CN$—30 ml of glacial acetic acid—870 ml of water

Flow rate: 2 ml/min, concentration: 0.25 mg/ml

Retention: 2.39 (85.7%; Z-isomer), 3.16 (11.3%; E-isomer).

Example 16

D-7-[(2-Aminobenzothiazol-6-yl)glycyl-amido]-3-[(Z)-1-propen-1-yl]-3-cephem-4-carboxylic acid

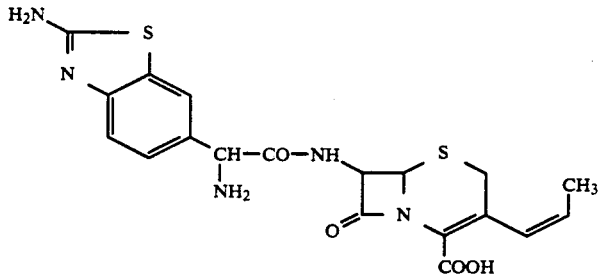

(a) Activation of the precursor acid 12.09 g [corresponds to 11.48 g (33.4 mmol)] of sodium D-α-[(1-methyl-2-methoxycarbonyl-vinyl)-amino]-(2-aminobenzothiazol-6-yl) acetate (content=95%, Example 14) are dissolved in 57 ml of dimethylformamide, and 23 ml of acetonitrile are then added. The solution is cooled to −70° C., 115 μl of 3-dimethylaminopropanol and 3.30 ml (34.4 mmol) of ethyl chloroformate are added in succession and the mixture is stirred at −70° C. for 20 minutes.

(b) Preparation of the cephalosporin component (7-APCA)

9.61 g (40 mmol) of 7-amino-3-[(Z)-1-propen-1-yl]-3-cephem-4-carboxylic acid (Example 15) are suspended in 57 ml of dimethylformamide and 23 ml of acetonitrile and the suspension is converted into a clear solution by addition of 1N sodium hydroxide solution (36.8 ml) to pH 8.5 at room temperature. The solution is cooled to −20° C. to −30° C.

(c) Coupling, deblocking and isolation of the crude betaine

The cooled 7-APCA solution (−20° C. to −30° C.) according to b) is slowly added dropwise to the solution of the mixed anhydride of the precursor acid according to a) at −70° C. and the mixture is subsequently stirred at −70° C. for 10 minutes. The temperature of the solution is then allowed to come to 0° C. (without cooling) in the course of 45 minutes and the solution is stirred with 1.2 g of active charcoal and 1.2 g of kieselguhr for a further 10 minutes. The reaction mixture is filtered over a Seitz filter, the residue on the filter is rinsed with a little dimethylformamide and 6.9 ml of concentrated hydrochloric acid are added to the filtrate. The volume of the solution is concentrated to 115 ml, salts which have precipitated out being separated off. The filtrate is brought to pH 4.0 by stirring with 25% strength NH3 solution with a magnetic stirrer and 800 ml of acetone are added, whereupon the crude betaine precipitates out. The precipitate is stirred for 10 minutes, filtered off with suction and rinsed with acetone and the material is dried in vacuo.

Yield: 12.65 g

Analytical HPLC: Hibar 250-4, Merck RP-8, 10 μm, 254 nm

Mobile phase: 100 ml of CH3CN—30 ml of glacial acetic acid—870 ml of water

Flow rate: 2 ml/min; concentration 1 mg/ml

Retention: 7.06 (73.8%; Z-isomer), 11.18 (11.5%; E-isomer).

The crude betaine is suspended in water and dissolved with half-concentrated hydrochloric acid at pH 1.2 and the solution is stirred with 1.2 g of active charcoal for 15 minutes. The mixture is filtered with suction over a kieselguhr bed, the residue on the filter is rinsed with 20 ml of 0.1N hydrochloric acid and the filtrate is pumped onto an RP 18 column (Hibar 250-25, Merck). The column is eluted first with water and then with 5% strength methanol. The fractions are investigated by means of analytical HPLC and the fractions which contain the Z-isomer derivative are combined, the methanol is distilled off in vacuo and the aqueous solution is lyophilized.

Yield: 5.2 g (32.3% of theory)

C19H19N5O4S2.2H2O (481.56)

Calculated: C 47.39, H 4.81, N 14.54, S 13.22. Found: C 47.7, H 4.8, N 14.3, S 13.0.

II.

D-7-[(2-Aminobenzothiazol-6-yl)glycyl-amido]-3-[(Z)-1-propen-1-yl]-3-cephem-4-carboxylic acid (different process)

(a) Activation of the precursor acid 100 g [corresponding to 95 g (0.277 mol) of pure material; 1.2 equivalents] of sodium D-α-[(1-methyl-2-methoxycarbonylvinyl)-amino]-(2-aminobenzothiazol-6-yl acetate (content=95%, Example 14) are dissolved in 500 ml of dimethylformamide and 200 ml of acetonitrile to give a clear solution. The solution is cooled to −60° C., 1 ml of 3-dimethylamino-1-propanol and 27.7 ml (0.281 mol) of ethyl chloroformate are added in succession and the mixture is stirred at −60° C. for 30 minutes.

(b) Preparation of the cephalosporin component 102 g (0.2304 mol) of benzhydryl 7-amino-3-[(Z)-1-propen-1-yl]-3-cephem-4-carboxylate hydrochloride (Example 10/II) are dissolved in 500 ml of dimethylformamide and 100 ml of acetonitrile to give a clear solution, 31 ml of water and 32.2 ml (0.2289 mol) of triethylamine are added at room temperature and the mixture is stirred for 5 minutes, while cooling with ice.

(c) Coupling

The cephalosporin solution (b), cooled to 0° C., is slowly added to the solution of the mixed anhydride (a) at −60° C., whereupon the temperature rises from −60° C. to −30° C. The mixture is subsequently stirred for a total of 30 minutes and the temperature of the reaction solution is allowed to come to 0° C. 57 ml of concentrated hydrochloric acid are then added and the solution is stirred at 0° C. for 15 minutes.

(d) Isolation of the trifluoroacetate salt

Acetonitrile is distilled off from the reaction solution and the pH is brought to 7.5 with 25% strength $NH_3$ solution, while cooling with ice. The solution is shaken in 5 l of ethyl acetate and 3 l of 10% strength $NaHCO_3$ solution containing sodium chloride. The mixture is stirred intensively for 5 minutes and then filtered with suction over a Seitz filter. The ethyl acetate phase is separated off and washed once with 4 l of saturated $NaHCO_3$ solution and twice with 4 l of water. Thereafter, the ethyl acetate phase is dried over $Na_2SO_4$, the drying agent is filtered off with suction and, finally, the filtrate is concentrated to dryness in vacuo. The rigid foam formed is dried under a high vacuum for 30 minutes. Yield: 170 g.

(e) Deblocking

The rigid foam is dissolved in 1,600 ml of $CH_2Cl_2$, the solution is cooled to 0° C. and a mixture of 750 ml of trifluoroacetic acid and 4 ml of anisole is added. The solution is then stirred at room temperature for 45 minutes and subsequently concentrated to an oil and the oily residue is digested with 6 l of ether. The material which has crystallized out is filtered off with suction, washed with ether and dried overnight in vacuo.

Yield: 125 g (97% of theory)

$C_{19}H_{19}N_5O_4S_2 \cdot CF_3COOH$ (559.55)

Analytical HPLC: Hibar 250-4, Merck RP-8, 254 nm

Mobile phase: 100 ml of $CH_3CN$—30 ml of glacial acetic acid—870 ml of water

Flow rate: 4 ml/min.

Retention: 2.25 (90.1%; Z-isomer), 3.77 (8.3%; E-isomer).

(f) Preparation in the pure form by means of adsorber resin chromatography 141 g of D-7-[(2-aminobenzothiazol-6-yl)glycylamido]-3-[(Z)-1-propen-1-yl]-3-cephem-4-carboxylic acid trifluoroacetate [moist material=128.8 g (100% of theory)] are suspended in 1,000 ml of water, the suspension is stirred intensively for 15 minutes and the insoluble material is then filtered off with suction and rinsed with water. The filtrate (pH 1.3) is introduced onto a column filled with 8 l of adsorber resin LGP 4429 (Lewatit OC 1062, BAYER AG). The column is eluted first with 5 l of water and then with in each case 2 l portions of water to which acetone is added in an amount which increases from 2% to 10%. A total of 15 fractions with a volume of in each case 2,000 ml are collected:

| Fraction (a = 2,000 ml) | Yield (g) |
| --- | --- |
| 1 | 3.5 |
| 2 | 2.1 |
| 3/4 | 9.5 |
| 5/6 | 16.7 |
| 7/8 | 13.2 |
| 9/10 | 8.3 |
| 11 | 5.1 |
| 12 | 5.3 |
| 13 | 3.7 |
| 14 | 2.3 |
| 15 | 1.0 |

Fractions 3 to 10, which contain the desired product in a highly pure form, are distilled in vacuo to remove the acetone and the residue is lyophilized.

Yield: 47.7 g (43.0% of theory)

$C_{19}H_{19}N_5O_4S_2 \cdot 2H_2O$ (481.56)

(g) Formation of the methanol solvate 168.3 g of D-7-[2-aminobenzothiazol-6-yl)glycylamido]-3-cephem-4-carboxylic acid as the lyophilizate (f) are stirred in 1,700 ml of methanol for 90 minutes, filtered off with suction and rinsed with 500 ml of methanol on the suction filter. The suction filter residue is stirred again in 1,000 ml of methanol for 45 minutes, filtered off with suction and rinsed with 500 ml of methanol on the suction filter. The product is dried overnight under a high vacuum.

Yield: 110.2 g (65.5% of theory); analytical HPLC: Hibar 250-4, Merck RP-8, 10 μm, 254 nm Mobile phase: 100 ml of $CH_3CN$—30 ml of glacial acetic acid—870 ml of water Flow rate: 4 ml $min^{-1}$; concentration: 1 mg $ml^{-1}$ Retention: 3.58 (98.4%; Z-isomer), 6.54 (0.79%; E-isomer).

(h) Formation on of the hydrate 109.6 g of D-7-[2-aminobenzothiazol-6-yl)glycylamido]-3-[(Z)-1-propen-1-yl-3-cephem-4-carboxylic acid methanol solvate (g) are introduced into 1,100 ml of water (obtained from Milli-Q Watersystem, Millipore GmbH), with stirring and the mixture is stirred with a magnetic stirrer in vacuo for 2 hours. The product is filtered off with suction and washed three times with approximately equal portions of water (from the Milli-Q Watersystem). The substance is dried under a high vacuum without a drying agent for 36 hours.

Yield: 94.7 g (86.4%)

$C_{19}H_{19}N_5O_4S_2 \cdot 2H_2O$ (463.541)

Calculated: C 49.23, H 4.57, N 15.11, S 13.83. Found: C 48.8, H 5.1, N 14.9, S 13.4.

Analytical HPLC: Hibar 250-4, Merck RP-8, 10 μm, 254 nm

Mobile phase: 100 ml of $CH_3CN$—30 ml of glacial acetic acid—870 ml of water

Flow rate: 4 ml $min^{-1}$; concentration: 1 mg $ml^{-1}$

Retention: 3.56 (98.8%).

Example 17

Sodium D-7-[(2-aminobenzothiazol-6-yl)glycyl-amido]-3-[(Z)-1-propen-1-yl]-3-cephem-4-carboxylate

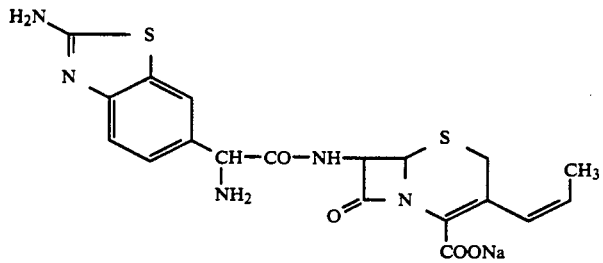

15.0 g (0.0324 mol) of D-7-[(2-aminobenzothiazol-6-yl)-glycyl-amido]-3-[(Z)-1-propen-1-yl]-3-cephem-4-carboxylic acid (Example 16/II) are suspended in 300 ml of water, with stirring, and the pH is brought to 8.56 under pH-stat conditions with 1N sodium hydroxide solution (Memo-Titrator DL 40 RC). The pale yellow solution formed is filtered with suction over filterpaper and the filtrate is lyophilized.

Yield: 15.0 g (92.1% of theory)
$C_{19}H_{18}N_5NaO_4S_2 \cdot 2H_2O$ (503.54)
Calculated: C 45.32, H 4.40, N 13.91, S 12.74, Na 4.56.
Found: C 46.0, H 4.9, N 14.0, S 12.9, Na 4.3.
NMR (DCOOD): $\delta = 1.64$ (dd, 3H); 3.38 (d,1H); 3.51 (d,1H; 5.26 (d, 1H); 5.72 (s, 1H); 5.78–5.85 (m, 1H); 5.85 (d, 1H); 6.21 (d, 1H); 7.76–7.83 (q, 2H); 8.12 (s, 1H) ppm.

Analytical HPLC: Hibar 250-4, RP-8, 10 μm, 254 nm
Mobile phase: 100 ml of $CH_3CN$—30 ml of glacial acetic acid—870 ml of water
Flow rate: 2 ml/min
Concentration: 1 mg/ml
Retention: 4.36 (content: 98.7%)

Example 18

D-α-t-Butoxycarbonylamino-α-(benzothiazol-6-yl)acetic acid

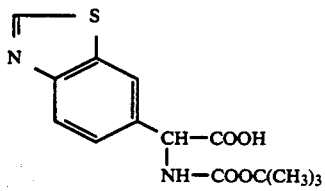

12.2 ml (0.102 mol) of tert.-butyl nitrite, dissolved in 25 ml of tetrahydrofuran, are added dropwise to a solution of 20 g (0.0618 mol) of D-α-t-butoxycarbonylamino-α-(2-aminobenzothiazol-6-yl)acetic acid in 160 ml of tetrahydrofuran at +50° C. to +60° C. in the course of 30 minutes. The mixture is subsequently stirred at 50° C. to +55° C. for 30 minutes, the solvent is distilled off and the residue is partitioned in 300 ml of water and 300 ml of ethyl acetate. The mixture is acidified to pH 1.5 with 2N HCl, while cooling with ice, and is stirred for 5 minutes and the pH is then brought to 8.0 to 8.5 with 40% strength potassium carbonate solution. The aqueous phase is separated off, washed again with ethyl acetate and then acidified to pH 2.5 with 2N HCl at 0° C. The acid solution is extracted twice with ethyl acetate and the extract is washed with sodium chloride solution and dried over sodium sulphate. The ethyl acetate phase is concentrated to 50 ml and stirred into petroleum ether.

Yield: 14.4 g (76% of theory)
$C_{14}H_{16}N_2O_4S$ (308.4)
Calculated: C 54.5, H 5.2, N 9.1, S 10.4. Found: C 54.1, H 5.6, N 8.9, S 9.7.
$[\alpha]_{589}^{20} = -130.3°$ C. (c=1, methanol)
NMR (DMSO): $\delta = 1.43$ (s, 9H); 5.31 (d, 1H); 7.6 (dd, 1H); 7.73 (d, 1H); 8.08 (d, 1H); 8.2 (weak d, 1H); 9.4 (s, 1H) ppm.

Example 19 p-Methoxybenzyl 7-phenylacetamido-3-[(Z)-propen-1-yl]-3-cephem-4-carboxylate

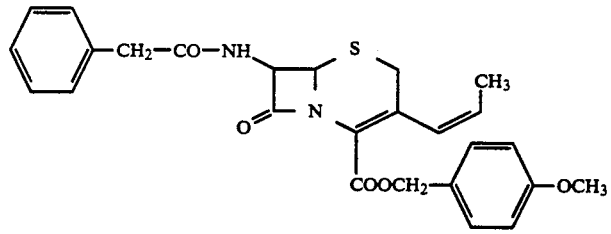

40.0 g (82.1 mmol) of p-methoxybenzyl 7-phenylacetamido-3-chloromethyl-3-cephem-4-carboxylate and 22.66 g (86.4 mmol) of triphenylphosphine are dissolved in 300 ml of dimethylformamide, 12.95 g (86.4 mmol) of sodium iodide are added and the mixture is stirred at room temperature for 2 hours. The reaction solution is then concentrated to an oil under a high vacuum.

The oily residue of 4.2 g is taken up in 130 ml of methylene chloride (no complete clear solution), 69.0 ml (1,231.5 mmol) of acetaldehyde are added to the mixture in a 500 ml three-necked flask and the mixture is then treated with 1N sodium hydroxide solution by means of an autotitrator at pH 8.1 under pH-stat conditions. After 1 hour, 8.7 ml of 1N sodium hydroxide solution have been consumed. A further 72.5 ml of 1N sodium hydroxide solution are then consumed at pH 8.3 in the course of 20 hours. The aqueous phase is separated off and the methylene chloride phase is washed twice with water and dried over sodium sulphate. The methylene chloride phase is then stirred again with 20 ml (358 mmol) of acetaldehyde at room temperature for 2 hours, the methylene chloride is distilled off, and the oil which remains is taken up in toluene and the mixture is introduced onto a column containing 1 l of silica gel (0.04–0.063 mm).

Elution is carried out first with toluene (fractions 1 to 5) and then with toluene/ethyl acetate (5:1, fractions 6, 7), 600 ml fractions being collected. Fractions 3 to 6 are combined and concentrated to dryness and the resulting oil is triturated with 100 to 150 ml of ether. The white material which has precipitated out is filtered off with suction and washed with ether (50 to 80 ml).

Yield: 12.1 g (31% of theory)

$C_{26}H_{26}N_2O_5S$ (478.6)

NMR (CDCl$_3$): $\delta = 1.52$ (d, 3H); 3.23 (d, 1H); 3.41 (d, 1H); 3.61 (q, 2H); 3.78 (s, 3H); 4.95 (d, 1H); 5.13 (s, 2H); 5.59–5.69 (dq, 1H); 5.75–5.81 (q, 1H); 6.08 (broad d, 1H); 6.45 (d, 1H); 6.87 (d, 2H); 7.25–7.36 (m, 7H) ppm.

Fractions 7 to 11 are concentrated to a slightly reddish oil, which cannot be assigned to the desired compound.

Example 20 p-Methoxybenzyl 7-amino-3-[(Z)-1-propen-1-yl]-3-cephem-4-carboxylate

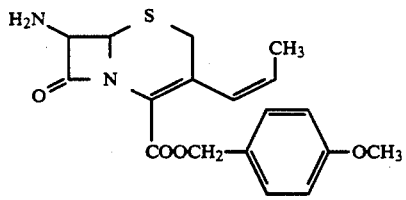

12.1 g (25.28 mmol) of p-methoxybenzyl 7-phenylacetamido-3-[(Z)-propen-1-yl]-3-cephem-4-carboxylate (Example 15) are dissolved in 133 ml of methylene chloride, the solution is cooled to −50° C. and 5.11 ml (63.2 mmol) of pyridine and 5.26 g (25.28 mmol) of phosphorus pentachloride are added in succession. The temperature is then allowed to rise to −10° C. in the course of 25 minutes. After a further 20 minutes, the temperature of the solution is 0° C.; thereafter, the solution is stirred to +15° C. for a further 45 minutes. The mixture is now cooled to −50° C., 200 ml of methanol (about −30° C.) are added all at once and the mixture is stirred for 30 minutes, without cooling. The reaction solution is concentrated, the oily residue is dissolved in methylene chloride and the solution is introduced onto a column packed with 400 ml of silica gel (0.04–0.063 mm). The column is eluted first with methylene chloride and then with the solvent mixtures methylene chloride—5% methanol and methylene chloride—10% methanol in succession. The fractions which are eluted with the methylene chloride—10% methanol mixture are concentrated to dryness.

Yield. 10 g

The oil is taken up in 500 ml of ethanol, an insoluble slime is separated off by decanting filtration, the filtrate is concentrated to dryness and the oil is dried in vacuo.

Yield: 6.8 g (75% of theory)

$C_{18}H_{20}N_2O_4S$ (360.4)

NMR (CDCl$_3$): $\delta = 1.55$ (dd, 3H); 1.95 (weak dd, 2H); 3.3 (d, 1H); 3.5 (d, 1H); 3.76 (s, 3H); 4.72 (d, 1H); 4.98 (d, 1H); 5.18 (s, 1H); 5.58–5.69 (dq, 1H); 6.1 (broad d, 1H); 6.88 (d, 2H); 7.31 (d, 2H); 8.61 (d, 1H) ppm.

Example 21 p-Methoxybenzyl D-7-[2-(t-butoxycarbonylamino)-2-(benzothiazol-6-yl)-glycylamido]-3-[(Z)-1-propen-1-yl]-3-cephem-4-carboxylate

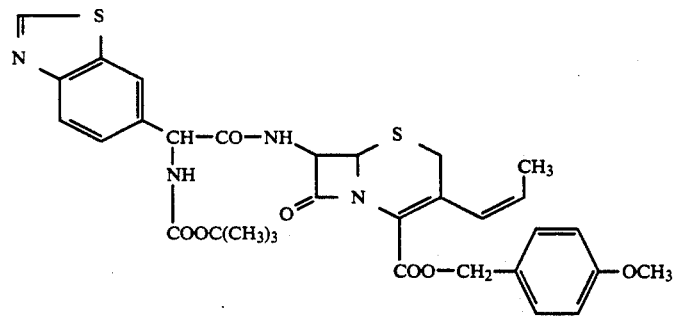

3.90 g (18.9 mmol) of dicyclohexylcarbodiimide are added to a solution of 5.83 g (18.9 mmol) of D-α-t-butoxycarbonylamino-α-(benzothiazol-6-yl)acetic acid and 6.8 g (15.1 mmol) of p-methoxybenzyl 7-amino-3-[(Z)-1-propen-1-yl]-3-cephem-4-carboxylate (Example 19) in 150 ml of tetrahydrofuran at room temperature, while stirring with a magnetic stirrer, and the mixture is then stirred for 2 hours. The dicyclohexylurea formed is filtered off with suction and washed with tetrahydrofuran and the mother liquor is concentrated to dryness. The oil which remains is dissolved in 100 ml of methylene chloride and the solution is chromatographed on 600 ml of silica gel (0.04–0.063 mm), elution being carried out first with methylene chloride (2×300 ml) and then with 5% strength methanol in methylene chloride with control by means of thin layer chromatography (methylene chloride: methanol=100:5). In each case 300 ml fractions are collected. The desired fractions of the eluate (11 and 12) with 5% strength methanol are combined and concentrated to dryness.

Yield: 8.8 g (89% of theory)

$C_{32}H_{34}N_4O_7S_2$ (650.8)

NMR (CDCl$_3$): $\delta = 1.4$ (s, 9H); 1.5 (dd, 3H); 3.12 (d, 1H); 3.32 (d, 1H); 3.75 (s, 3H); 4.91 (d, 1H); 5.13 (s and d, 3H); 5.58–5.68 (m, 1H); 5.73–5.79 (q, 1H); 6.03 (broad d, 1H); 6.86 (d, 2H); 7.28 (d, 2H); 7.52 (d, 1H); 8.01 (s, 1H); 8.1 (d, 1H); 9.4 (s, 1H) ppm.

Example 22

D-7-[(Benzothiazol-6-yl)glycylamido]-3-[(Z)-1-propen-1-yl]-3-cephem-4-carboxylic acid

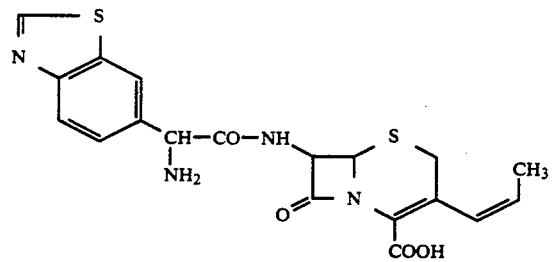

A mixture of 8.8 g (13.5 mmol) of p-methoxybenzyl D-7-[2-(t-butoxycarbonylamino)-2-(benzothiazol-6-yl)glycylamido]-3-[(Z)-1-propen-1-yl]-3-cephem-4-carboxylate (Example 20), 3 ml of anisole and 100 ml of trifluoroacetic acid is stirred at room temperature for 1 hour. The mixture is concentrated in vacuo, 40 ml of toluene are added to the pale red, readily mobile oil and the mixture is concentrated again in vacuo. The oil which remains is triturated with 400 ml of ether and the solid which has precipitated out is filtered off with suction, washed with ether and dried in vacuo. 6.3 g of trifluoroacetate are obtained and are dissolved in 800 ml of water, and the insoluble constituents are separated off by filtration over kieselguhr. The solution is passed over an HP 20 column (600 ml, Diaion adsorber resin, Mitsubishi), which is eluted with water and then with a mixture of water and methanol (gradient up to 50%). The eluate containing the desired compound is lyophilized.

Yield: 1.9 g

The lyphilizate is dissolved almost completely in 150 ml of water, while stirring with a magnetic stirrer, 100 mg of active charcoal are added, the mixture is stirred for 5 minutes and the solid is then filtered off with suction over kieselguhr and rinsed with 50 ml of water. The filtrate is filtered again with a syringe by means of a Millipore membrane filter and is then pumped onto a preparative column (Hibar 250-25, RP-18, Merck, flow rate: 10-15 ml. minute$^{-1}$). After application of the sample, the column is eluted with the following mobile phase systems in succession:
1. 500 ml of water
2. 500 ml of water with 10% of methanol
3. 1,000 ml of water with 10% to 40% of methanol: the eluate is collected here in 50-100 ml fractions and then investigated by means of analytical HPLC, it being found that fractions 8 to 10 contain the cis-isomer derivative.

Yield: 468 mg $C_{19}H_{18}N_4O_4S_2$ (430.5)

NMR (DCOOD): $\delta = 1.61$ (dd, 3H); 3.31 (d, 1H); 3.48 (d, 1H); 5.25 (d, 1H); 5.75-5.9 (m and q, 3H); 6.2 (broad d, 1H); 8.13 (dd, 1H); 8.48 (d, 1H); 8.67 (s, 1H); 10.33 (s, 1H); ppm.

Analytical HPLC: Hibar 250-4, RP-8, 10 μm, 254 nm

Mobile phase system: 790 ml of water—200 ml of methanol—10 ml of buffer, pH 7.0

Flow rate: 2 ml/min, concentration: 1 mg/ml
Retention: 7.53 (content: 92.4%)

Example 23

D-7-[(2-Aminobenzothiazol-6-yl)glycylamido]-3-vinyl-3-cephem-4-carboxylic acid

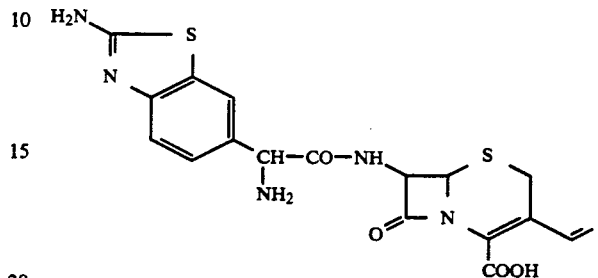

276.1 μl (1.585 mmol) of ethyl diisopropylamine and 122.7 μl (1.585 mmol) of mesyl chloride are slowly injected in succession into a solution, cooled to $-50°$ C., of 512.5 mg (1.585 mmol) of D-α-t-butoxycarbonylamino-α-(2-aminobenzothiazol-6-yl)acetic acid in 5 ml of dimethylformamide. The mixture is stirred at $-50°$ C. for 40 minutes and a solution ($-20°$ C.) of 622 mg (1.585 mmol) of diphenylmethyl 7-amino-3-vinyl-3-cephem-4-carboxylate and 276.1 μl (1.585 mmol) of ethyldiisopropylamine in 5 ml of tetrahydrofuran and 3 ml of dimethylformamide is added dropwise. The mixture is subsequently stirred at $-50°$ C. for 5 minutes and then without cooling for a further 50 minutes. Thereafter, the reaction solution is stirred into 40 ml of water and 120 ml of ethyl acetate, the ethyl acetate phase is separated off, the aqueous layer is extracted again with 60 ml of ethyl acetate and the organic phases are combined and washed with 0.1N hydrochloric acid, sodium bicarbonate solution and sodium chloride solution. After drying and distilling off the solvent, the residue is taken up in 20 ml of methylene chloride, 20 ml of trifluoroacetic acid with 1 drop of anisole are added and the mixture is stirred at room temperature for 45 minutes. The trifluoroacetic acid/methylene chloride mixture is then distilled off in vacuo, the residue is dissolved in 15 ml of 80% strength acetic acid, the solution is pumped onto an RP-18 column (Hibar 250-25, Merck) and the column is eluted with 3% strength acetic acid. The eluate, which contains the desired substance, is freeze-dried.

Yield: 800 mg

The lyophilizate is dissolved again in 10 ml of 3% strength acetic acid and the solution is rechromatographed on an RP-18 column (Hibar 250-25, Merck).

Yield: 165 mg $C_{18}H_{17}N_5O_4S_2 \cdot 3H_2O \cdot \frac{1}{2}CH_3COOH$ (505.5)

NMR (DCOOD): $\delta = 3.61-3.76$ (dd, 2H); 5.28 (d, 1H); 5.52 (d, 1H); 5.69 (d, 1H); 5.75 (s., 1H); 5.91 (d, 1H); 7.18-7.28 (q, 1H); 7.84 (m, 2H); 8.18 (s, 1H) ppm.

Example 24

Benzhydryl D-7-[2-(t-butoxycarbonylamino)-2-(2-aminobenzothiazol-6-yl)glycylamido]-3-[(Z)-2-cyclopropylvinyl]-3-cephem-4-carboxylate

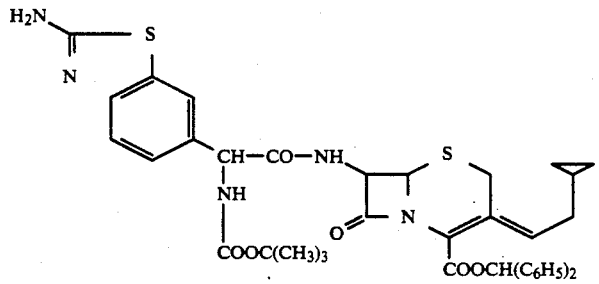

6.34 g (0.091 mol) of cyclopropanecarboxaldehyde and 7.6 g (0.007 mol) of benzhydryl D-7-[2-(t-butoxycarbonylamino)-2-(2-aminobenzothiazol-6-yl)glycylamido]3-(triphenylphosphonio)methyl-3-cephem-4-carboxylate iodide (Example 4) are added to a cold solution of 6.08 g (0.07 mol) of lithium bromide in 50 ml of dimethylformamide and 150 ml of methylene chloride at −5° C. The mixture is stirred at −5° C. for 20 hours and then at room temperature for 5 hours. The solution is concentrated to about 50 ml in vacuo and the concentrate is partitioned between a solvent mixture of 200 ml of ethyl acetate and 200 ml of water. The upper layer is separated off and washed once with aqueous sodium chloride solution. After drying over sodium sulphate and distilling off the solvent, the residue is taken up in toluene and introduced onto a column packed with silica gel (0.04–0.063 mm). The column is eluted first with toluene and then with the solvent mixture toluene/ethyl acetate (5:1) and toluene/ethyl acetate (1:1).

Yield: 3.0 g (57.5% of theory)
$C_{39}H_{37}N_5O_6S_2$ (737.9)
Calculated: C 63.48, H 5.33, N 9.49, S 8.69.
Found: C 62.8, H 5.01, N 9.18, S 7.93.

Example 25

D-7-[(2-Aminobenzothiazol-6-yl)glycylamido]-3-[(Z)-2-cyclopropyl-vinyl]-3-cephem-4-carboxylic acid, cis-isomer

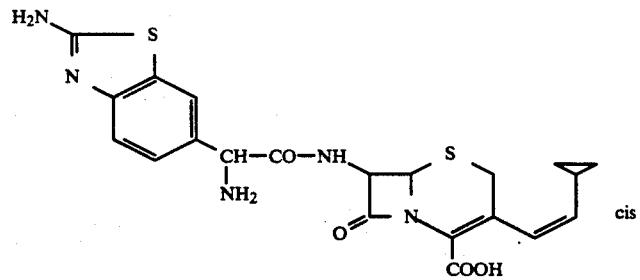

2.9 g (3.9 mmol) of benzhydryl D-7-[2-(t-butoxycarbonylamino)-2-(2-aminobenzothiazol-6-yl)glycylamido]3-[(Z)-2-cyclopropyl-vinyl]-3-cephem-4-carboxylate (Example 24) are dissolved in 20 ml of methylene chloride, 40 ml of trifluoroacetic acid (TFA) are added and the mixture is stirred with a magnetic stirrer at room temperature for 60 minutes. The methylene chloride and trifluoroacetic acid are removed in vacuo, the semi-solid red oil which remains is triturated in ether and the product is filtered off with suction and washed with ether. The pale yellow trifluoroacetate is dried in vacuo and then suspended in 100 ml of water and insoluble yellow flocks are filtered off with suction over kieselguhr and rinsed again with 30 ml of water.

The still slightly cloudy solution is filtered again over a membrane filter (Millipore, 0.45 μm). The filtrate is pumped onto an RP 18 column (Hibar 250-25, Merck). The column is eluted first with 200 ml of water (fraction 1), then with 400 ml of 5% strength methanol (fraction 2) and finally with 10% strength methanol, in each case 300 ml fractions being collected (fractions 3 to 12).

The fractions are investigated by means of analytical HPLC and fractions 6 to 10, which contain the desired peak, are combined, the methanol is distilled off in vacuo and the residue is lyophilized.

Yield: 480 mg (25.9% of theory)
$C_{21}H_{21}N_5O_4S_2$ (471.5)
NMR (DCOOD): δ=0.48 (m, 2H); 0.81 (m, 2H); 1.37–1.48 (m, 1H); 3.48–3.68 (q, 2H); 5.1–5.18 (t, 1H); 5.28 (d, 1H); 5.72 (s, 1H); 5.82 (d, 1H); 6.15–6.2 (d, 1H); 7.8 (q, 2H); 8.12 (s, 1H) ppm.

Example 26

Benzhydryl 7-phenylacetamido-3-[(Z)-2-cyclopropyl-vinyl]-3-cephem-4-carboxylate

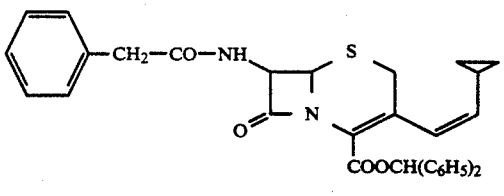

15.9 g (17.9 mmol) of benzhydryl 7-phenylacetamido-3-(triphenylphosphonio)methyl-3-cephem-4-carboxylate iodide (Example 7) are taken in 100 ml of methylene chloride and 17.56 g (250.6 mmol)

of cyclopropanecarboxaldehyde in a 250 ml three-necked flask. The mixture is cooled to 0° C. and 100 ml of water are added. 16.3 ml of 1N NaOH are then added dropwise in the course of 4 hours, the pH being kept constant at 8.6. The reaction solution is diluted with methylene chloride and the organic phase is separated off, washed once with water and then dried over sodium sulphate. After the drying agent has been removed, a further 13 ml (233 mmol) of cyclopropanecarboxaldehyde are added to the methylene chloride solution and the mixture is stirred overnight. The reaction solution is then concentrated to dryness, the residue is again dissolved in a little methylene chloride and the mixture is introduced onto a column filled with 500 ml of silica gel (0.04–0.063 mm). 400 ml fractions are collected and all the fractions are investigated for the cis-isomer compound by means of analytical HPLC.

Yield: 4.5 g (45.6% of theory)

$C_{33}H_{30}N_2O_4S$ (550.7)

Calculated: C 71.97, H 5,49, N 5.09, S 4.58. Found: C 70.5, H 5.11, N 4.81, S 4.05.

NMR (CDCl₃): δ=0.19–0.25 (m, 1H); 0.34–0.42 (m, 1H); 0.63–0.78 (mm, 2H); 1.24–1.35 (m, 1H); 3.4–3.6 (dd, 2H); 3.66 (q, 2H); 4.87–4.93 (t, 1H); 5.01 (d, 1H); 5.77–5.81 (q, 1H); 6.08–6.12 (d, 1H); 6.15 (d, 1H); 6.93 (s, 1H); 7.27–7.41 (mm, 15H) ppm.

Example 27

7-Phenylacetamido-3-[(Z)-2-cyclopropylvinyl]-3-cephem-4-carboxylic acid

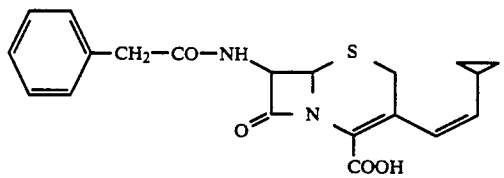

12.5 g (0.0227 mmol) of benzhydryl 7-phenylacetamido-3-[(Z)-2-cyclopropyl-vinyl]-3-cephem-4-carboxylate are dissolved in 23 ml of methylene chloride with the addition of 7.2 ml of anisole, the solution is cooled to 0° C. and 23 ml of trifluoroacetic acid are added. The mixture is stirred at 0° C. for 30 minutes and 46 ml of water are then added. 400 ml of diisopropyl ether are subsequently added to he reaction solution and the mixture is stirred at 0° C. for 30 minutes. The product which has crystallized out is filtered off with suction and washed with diisopropyl ether.

Yield: 6.9 g (79.1% of theory)

$C_{22}H_{20}H_2O_4S$ (384.45)

NMR (DMSO): δ=0.39–0.47 (m, 2H); 0.75–0.83 (m, 2H); 1.44–1.60 (m, 1H); 3.55 (d, 2H); 3.61 (d, 1H); 3.77 (d, H); 4.93–5.04 (m, 1H); 5.16 (d, 1H); 5.59–5.69 (q, 1H); 6.08–6.15 (d, 1H); 7.20–7.35 (m, 5H) ppm.

Example 28

7-Amino-3-[(Z)-2-cyclopropyl-vinyl]-3-cephem-4-carboxylic acid

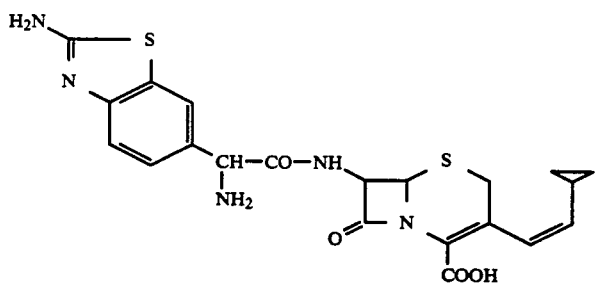

6 g (0.0156 mol) of 7-phenylacetamido-3-[(Z)-2-cyclopropyl-viny]-3-cephem-4-carboxylic acid are suspended in 320 ml of water and the suspension is brought to pH 7.8 with half-concentrated ammonia solution, whereupon an almost clear solution forms. The solution is warmed to 37° C. and 35 g of penicillin-acylase resin are added. The reaction solution is titrated further to pH 7.8 with ammonia and kept at 37° C. for 5 hours. The resin is then filtered off with suction and the filtrate is concentrated down to a volume of 50 ml. The concentrated solution is brought to pH 4.2 with 2N HCl, whereupon the product precipitates out and is filtered off with suction and washed with water and acetone.

Yield: 3.6 g (86.7% of theory)

$C_{22}H_{14}N_2O_3S$ (266.32)

NMR (DCOOD): δ=0.53–0.61 (m, 2H); 0.88–0.98 (m, 2H); 1.45–2.0 (m, 1H); 3.58 (d, 1H); 3.72 (d, 1H); 5.25–5.38 (t, 1H); 5.39 (d, 1H); 5.48 (d, 1H); 6.44–6.50 (d, 1H) ppm.

Example 29

D-7-[(2-Aminobenzothiazol-6-yl)glycylamido]-3-[(Z)-2-cyclopropyl-vinyl]-3-cephem-4-carboxylic acid, cis-isomer (a) Activation of the precursor acid 4.12 g [corresponds to 3.54 g (0.0103 mol) of pure substance] of sodium D-α-[(1-methyl-2-methoxycarbonyl-vinyl)-amino]-(2-amino-benzothiazol-6-yl)acetate (content: 86%) are dissolved in 30 ml of dimethylformamide and 10 ml of acetonitrile to give a clear solution. The solution is cooled to −70° C., 5 drops of 3-dimethylaminopropanol aminopropanol and 1.0 ml (0.0104 mol) of ethyl chloroformate are added and the mixture is stirred at −60° C. for 30 minutes.

(b) Preparation of the cephalosporin component 2.5 g (9.39 mmol) of 7-amino-3-[(Z)-2-cyclopropyl-vinyl]-3-cephem-4-carboxylic acid are suspended in 20 ml of dimethylformamide and 7 ml of acetonitrile and the suspension is cooled to 0° C. and converted into a clear solution by addition of 1N sodium hydroxide solution (about 9 ml) to pH 8.5. The solution is cooled to −50° C.

(c) Coupling, deblocking and isolation of the crude betaine

The cooled cephalosporin solution (b) is added to the solution of the mixed anhydride of the precursor acid (a) at −60° C. The temperature is then allowed to rise to −10° C. in the course of 90 minutes (without a cooling bath) and the solution is additionally stirred with 500 mg of active charcoal and 500 mg of kieselguhr for a further 10 minutes, whereupon the temperature rises up to +10° C. The reaction mixture is filtered over a Seitz filter, the residue is rinsed with a little dimethylformamide, and 2 ml of concentrated hydrochloric acid are added to the filtrate at 0° C. After 15 minutes, the solution is concentrated in vacuo and the salt which has precipitated out is filtered off with suction and rinsed with a little dimethylformamide. The filtrate is brought to pH 4.6 with 25% strength ammonia solution and is then stirred into 500 ml of acetone, whereupon the crude betaine precipitates out. The precipitate is filtered off with suction and rinsed with acetone and the material is dried in vacuo.

Yield: 6.1 g d) Chromatography

The crude betaine is suspended in 80 ml of water and the pH is brought to 1.4 with 2N HCl (clear solution). The solution is introduced onto a column filled with 800 ml of adsorber resin LPG 4429 (Lewatit ® OC 1062, particle size 0.1 to 0.5 mm, BAYER) The column is first eluted with 1,300 ml of water. The column is then washed with water, to which an increasing content of acetone of 0% to 20% is continuously added. A total of 18 fractions of 200 ml of eluate are collected, fractions 9-15 containing the desired compound, according to analytical HPLC control. The fractions with the Z-isomer are combined, the acetone is distilled off in vacuo and the aqueous filtrate is lyophilized.

Yield: 1.42 g (29% of theory)
$C_{21}H_{21}N_5O_4S_2 \cdot 3H_2O$ (525.61)
Calculated: C 48.0, H 5.18, N 13.32, S 12.20. Found: C 47.9, H 5.0, N 12.5, S 11.7.

NMR (DMSO): δ=0.48 (narrow m, 2H); 0.81 (narrow m, 2H); 1.37-1.48 (m, 1H); 3.48-3.68 (q, 2H); 5.1-5.18 (t, 1H); 5.28 (d, 1H); 5.72 (s, 1H); 5.82 (d, 1H); 6.15-6.2 (d, 1H); 7.8 (q, 2H); 8.12 (s, 1H) ppm.

Example 30

Benzhydryl 7-phenylacetamido-3-[(triphenylphosphoranylidene)-methyl]-3-cephem-4-carboxylate

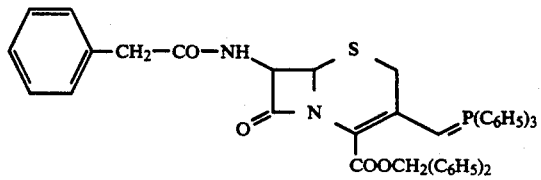

14.0 g (0.132 mol) of $Na_2CO_3$, dissolved in 150 ml of water, are added to a suspension of 78.0 g (0.088 mol) of benzhydryl 7-phenylacetamido-3-(triphenylphosphonio)methyl-3-cephem-4-carboxylate iodide (Example 7) in 400 ml of methylene chloride and the mixture is stirred vigorously at room temperature for 15 minutes. The $CH_2Cl_2$ layer is separated off, the aqueous phase is extracted again with 200 ml of $CH_2Cl_2$ and the combined organic phases are dried over sodium sulphate. The methylene chloride phase is concentrated to dryness and the residue is stirred in about 600 ml of acetone for 1 hour. The product is filtered off with suction and rinsed thoroughly with acetone.

Yield: 58.9 g (88.3% of theory)
$C_{47}H_{39}N_2O_4SP$ (758.8)
NMR (DMSO) δ=2.4 (d, 1H); 3.2 (d, 1H); 3.49 (s, 2H); 5.1 (d, 1H); 5.19-5.24 (q, 1H); 5.43 (d, 1H); 6.75 (s, 1H); 7.2-7.49 (broad m, 15H); 7.62-7.78 (m, 15H); 8.84 (d, 1H) ppm.

Example 31

Benzhydryl 7-phenylacetamido-3-[(Z)-3-(3,3,3-trifluoropropenyl]-3-cephem-4-carboxylate

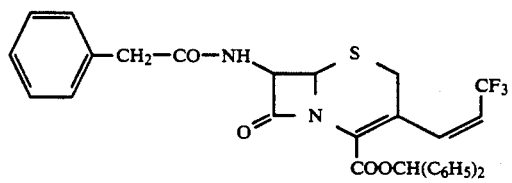

A solution of 385 ml of methylene chloride and 8.5 ml of methanol, to which 257 mg (1.13 mmol) of p-benzoylbenzoic acid have been added, is cooled to +8° C. 32.5 g (0.332 mol) of trifluoroacetaldehyde are added in the course of 10 minutes, whereupon the temperature of the solution is allowed to rise to +15° C. 5 minutes after the addition, 12.6 g (0.0166 mol) of benzhydryl 7-phenylacetamido-3-[(triphenylphosphoran-ylidene)methyl]-3-cephem-4-carboxylate (Example 30) are added, the low temperature bath is removed and the mixture is stirred at +35° C. with exclusion of light and under nitrogen for 4 hours. The dark red solution is then concentrated to dryness and ether is added to the oil which remains, crystallization gradually starting.

Yield: 6.2 g (64.6% of theory)
$C_{31}H_{25}F_3N_2O_4S$ (578.6)
Calculated: C 64.35, H 4.36, N 4.84, S 5.54, F 9.85. Found: C 63.72, H 4.10, N 4.27, S 5.02, F 9.27.

Example 32

Benzhydryl 7-amino-3-[(Z)-3-(3,3-trifluoro-propenyl]-3-cephem-4-carboxylate

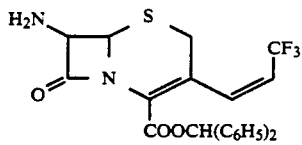

6.0 g (0.0104 mol) of benzhydryl 7-phenylacetamido-3-[(Z)-3-(3,3,3-trifluoropropenyl]-3-cephem-4-carboxylate (Example 31) are dissolved in 64 ml of methylene chloride, the solution is cooled to −40° C. with a dry ice bath and 2.1 ml (0.026 mol) of pyridine and 2.17 g (0.0104 mol) of phosphorus pentachloride are added in succession. After 5 minutes, the mixture is allowed to warm to −20° C., and thereafter the temperature should rise to −10° C. in the course of 20 minutes and finally to +10° C. The solution is now stirred at +10° C. to +15° C. for 1 hour. The mixture is subsequently cooled to −40° C., 70 ml of methanol (−30° C.) are added and the mixture is stirred at +10° C. for a further 30 minutes. The reaction solution is concentrated gently, the oil which is obtained is dissolved in 600 ml of methylene chloride, the solution is stirred into 800 ml of sodium bicarbonate solution and the mixture is stirred for 10 minutes. The methylene chloride phase is separated off, washed once with water and dried over sodium sulphate. The methylene chloride filtrate is chromatographed on 400 ml of silica gel (0.04–0.063 mm), elution being carried out first with methylene chloride and then with methylene chloride with the addition of methanol (gradient up to 10%). The eluate is investigated by means of analytical HPLC and thin layer chromatography (TLC: methylene chloride/methanol=100:1).

Yield: 3.4 g (71.1% of theory)

$C_{23}H_{19}F_3N_2O_3S$ (460.5)

NMR (CDCl$_3$): δ=3.3 (d, 1H); 3.48 (d, 1H); 4.75 (d, 1H); 4.98 (d, 1H); 5.45–5.55 (d-q, 1H); 6.07 (d, 1H); 6.96 (s, 1H); 7.23–7.42 (m, 10H); 8.6 (d, 2H) ppm.

Example 33

7-Amino-3-[(Z)-3-(3,3,3-trifluoro-propenyl]-3-cephem-4-carboxylic acid

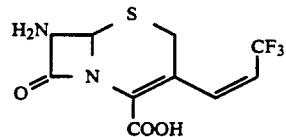

3.1 q (6.73 mmol) of benzhydryl 7-amino-3-[(Z)-3-(3,3,3-trifluoropropenyl]-3-cephem-4-carboxylate (Example 32) are added to a stirred solution of 30 ml of trifluoroacetic acid (TFA) and 1.5 ml of anisole, which is cooled to 0° C. The mixture is stirred at room temperature for 1 hour and then concentrated at 30° C. in vacuo and the oily residue is stirred with 100 ml of ether for 1 hour. The precipitate is filtered off with suction and washed with 50 ml of ether and the residue on the filter is dried in vacuo for 3 hours. The trifluoroacetate is suspended in 20 ml of water, the suspension is cooled to +5° C. and the pH is brought to 0.2–0.4 with 12N HCl. The clear solution formed is cooled to +5° C. and stirred with 300 mg of active charcoal for 10 minutes. The mixture is filtered with suction over kieselguhr and the residue is rinsed with about 20 ml of 0.1N HCl. The filtrate is brought to pH 2.1 with 20% strength NaOH at +5° C. and the product which has precipitated out is left to stand in a refrigerator for 1 hour in order to bring the crystallization to completion. The crystal sludge is filtered off with suction, washed with 20 ml of water and 80 ml of acetone and dried in vacuo Yield: 1.45 g (73.2% of theory)

$C_{10}H_9F_3N_2O_3S$ (294.3)

Calculated: C 40.81, H 3.08, N 9.52, S 10.89, F 19.37.
Found: C 39.60, H 2.91, N 9.02, S 10.18, F 18.52.

Example 34

D-7-[(2-Aminobenzothiazol-6-yl)glycyl-amido]-3-[(Z)-3(3,3,3-trifluoro-propenyl]-3-cephem-4-carboxylic acid, cis-isomer

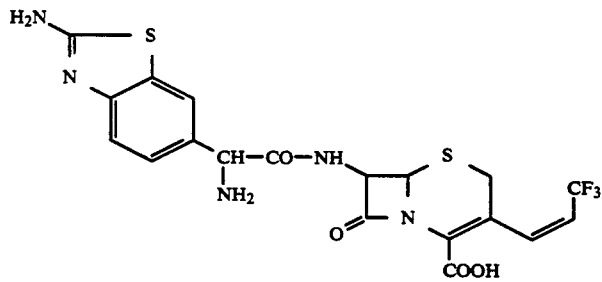

(a) Activation of the precursor acid 1.72 g [corresponds to 1.63 g (4.75 mmol)] of sodium D-α-[(1-methyl-2-methoxycarbonyl-vinyl)-amino]-(2-aminobenzothiazol-6-yl)acetate (content=95%) are dissolved in 15 ml of dimethylformamide and the solution is then diluted with 7 ml of acetonitrile. The solution is cooled to −70° C., 40 μl of 3-dimethylaminopropanol and 0.456 ml (4.75 mmol) of ethyl chloroformate are added in succession and the mixture is stirred at −70° C. for 20 minutes.

(b) Preparation of the cephalosporin component 1.4 g (4.75 mmol) of 7-amino-3-[(Z)-3-(3,3,3-trifluoropropenyl]-3-cephem-4-carboxylic acid (Example 33) are suspended in 15 ml of dimethylformamide and 7 ml of acetonitrile and the suspension is converted into a clear solution by addition of 1N sodium hydroxide solution (4.2 ml) to pH 8.5 at room temperature. The solution is cooled to −20° C. to −30° C.

(c) Coupling, deblocking and isolation of the crude betaine

The cooled solution of the 3-trifluoropropenylcephalosporin b) (−20° C.) is slowly added dropwise to the solution of the mixed anhydride of the precursor acid according to a) at −70° C. and the mixture is subsequently stirred at −70° C. for 10 minutes. The temperature of the solution is then allowed to come to 0° C. in the course of 45 minutes (without cooling) and the solution is stirred with 150 mg of active charcoal and 500 mg of kieselguhr for a further 10 minutes. The reaction mixture is filtered over a Seitz filter, the residue is rinsed with a little dimethylformamide, and 1 ml of concentrated hydrochloric acid is added to the filtrate. The volume of the solution is concentrated to 25 ml, the salts which have precipitated out being separated off. The filtrate is brought to pH 4.0 with 25% strength $NH_3$ solution, while stirring with a magnetic stirrer, and 100 ml of acetone are added, whereupon the crude betaine precipitates out The precipitate is stirred for 10 minutes, filtered off with suction and rinsed with acetone and the material is dried in vacuo.

Yield: 1.9 g (74.5% of theory)

The crude betaine is suspended in-water and dissolved with half-concentrated hydrochloric acid at pH 1.2 and the solution is stirred with 190 mg of active charcoal for 15 minutes. The mixture is filtered with suction over a kieselguhr bed, the residue is rinsed with 15 ml of 0.1N hydrochloric acid and the filtrate is pumped onto an RP 18 column (Hibar 250-25, Merck). The column is eluted first with water and then with 5% strength methanol. The fractions are investigated by means of analytical HPLC and the fractions which contain the Z-isomer derivative are combined, the methanol is distilled off in vacuo and the aqueous solution is lyophilized.

Yield: 520 mg (31.7% of theory)
$C_{19}H_{16}F_3N_5O_4S_2 \cdot 2H_2O$ (535.5)

NHR (DCOOD): δ=3.21 (d, 1H); 3.52 (d, 1H); 5.19 (d, 1H); 5.78–5.91 (m, 3H); 6.25 (d, 1); 7.81–7.9 (q, 2H); 8.18 (s, 1H) ppm.

Example 35

D-7-[(2-Aminobenzothiazol-6-yl)glycylamido]-3-[(E)-3-(3,3,3-trifluoropropenyl]-3-cephem-4-carboxylic acid, trans-isomer

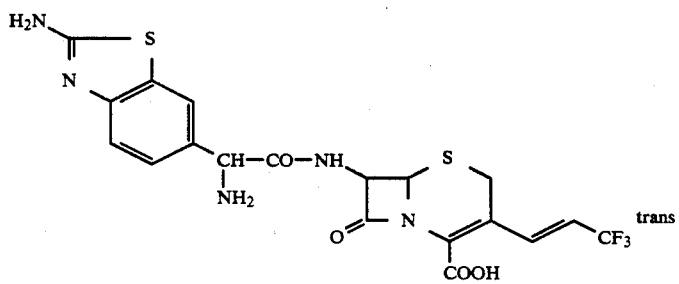

The trans-isomer compound is obtained as a by-product from the methanol-containing eluates of Example 34 by preparative HPLC separation on a Hibar column, RP-18.

IR: Nujol v max. 1780, 1690, 1620, 1520, 1470, 1380, 1350, 1280 cm$^{-1}$

Example 38

D-7-[(2-Aminobenzothiazol-6-yl)glycylamido]-3-[2-(3-pyridyl)vinyl]-3-cephem-4-carboxylic acid, cis-isomer

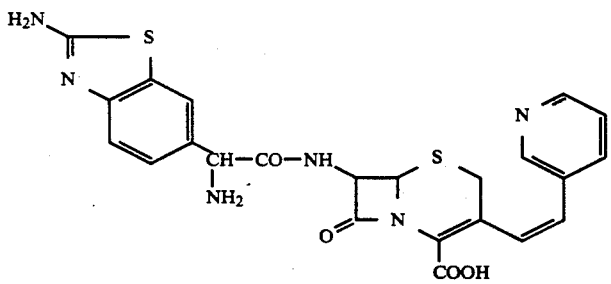

Analogously to Example 34, 1.6 g, corresponding to 1.52 g (4.43 mmol) of sodium D-α-[(1-methyl-2-methoxycarbonyl-vinyl)-amino[-( 2-aminobenzothiazol-6-yl)acetate (content: 95%) are activated with 0.425 ml (4.43 mmol) of ethyl chloroformate with catalytic amounts of 3-dimethylaminopropanol in dimethylformamide/acetonitrile and reacted with a solution of 1.34 g (4.43 mmol) of 7-amino-3-[2-(3-pyridyl)vinyl]-3-cephem-4-carboxylic acid in dimethylformamide/acetonitrile and sodium hydroxide solution (1N).

After isolation of the crude betaine analogously to Example 16, the cis-isomer compound is purified with the aid of preparative HPLC.

Yield: 735 mg (30.5% of theory)
$C_{23}H_{20}N_6O_4S_2 \cdot 2H_2O$ (544.6)

IR (Nujol), max.: 1775, 1690, 1620, 1530 cm$^{-1}$.

It is understood that the specification and examples are illustrative but not limitative of the present invention and that other embodiments within the spirit and scope of the invention will suggest themselves to those skilled in the art.
We claim:
1. D-7-[(2-aminobenzothiazol-6-yl)glycylamido]-3-[2-cyclopropyl-vinyl]-3-cephem-4-carboxylic acid of the formula
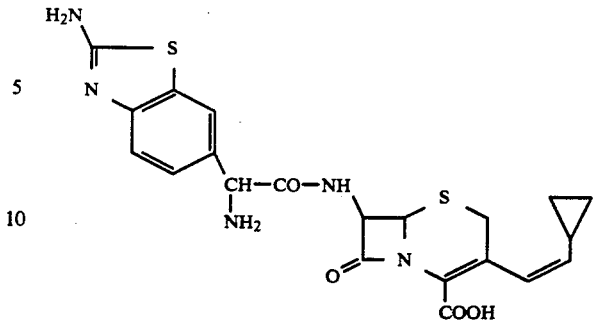
or a salt thereof.
2. D-7-[(2-aminobenzothiazol-6-yl)glycylamido]-3-[(Z)-1-propen-1-yl]-3-cephem-4-carboxylic acid of the formula
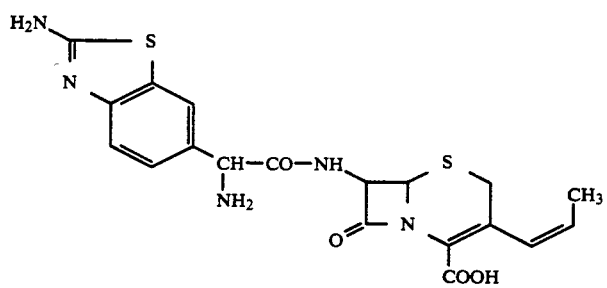
or a salt thereof.
* * * * *